US011426489B2

(12) United States Patent
Klimek et al.

(10) Patent No.: US 11,426,489 B2
(45) Date of Patent: Aug. 30, 2022

(54) BIOMATERIAL COMPOSITIONS, IMPLANTS, AND METHODS OF MAKING THE SAME

(71) Applicant: GLOBUS MEDICAL, INC., Audubon, PA (US)

(72) Inventors: Jennifer Klimek, King of Prussia, PA (US); Archana Bhat, Phoenixville, PA (US); Vipin Kunjachan, Audubon, PA (US); Chris Geisler, Philadelphia, PA (US); Allison Adams, Philadelphia, PA (US); Christine Grimes, Jeffersonville, PA (US)

(73) Assignee: Globus Medical, Inc., Audubon, PA (US)

( * ) Notice: Subject to any disclaimer, the term of this patent is extended or adjusted under 35 U.S.C. 154(b) by 285 days.

(21) Appl. No.: 14/810,858

(22) Filed: Jul. 28, 2015

(65) Prior Publication Data
US 2016/0361467 A1    Dec. 15, 2016

Related U.S. Application Data

(63) Continuation-in-part of application No. 14/735,460, filed on Jun. 10, 2015, now Pat. No. 10,016,529.

(51) Int. Cl.
| | | |
|---|---|---|
| A61L 31/02 | (2006.01) | |
| A61L 27/54 | (2006.01) | |
| A61L 27/36 | (2006.01) | |
| A61L 27/42 | (2006.01) | |
| A61L 27/56 | (2006.01) | |
| A61F 2/44 | (2006.01) | |
| A61F 2/28 | (2006.01) | |
| A61L 27/10 | (2006.01) | |
| A61L 27/12 | (2006.01) | |
| A61L 27/50 | (2006.01) | |
| A61F 2/30 | (2006.01) | |

(52) U.S. Cl.
CPC ............ *A61L 27/3608* (2013.01); *A61F 2/28* (2013.01); *A61F 2/2846* (2013.01); *A61F 2/447* (2013.01); *A61F 2/4455* (2013.01); *A61L 27/10* (2013.01); *A61L 27/12* (2013.01); *A61L 27/427* (2013.01); *A61L 27/50* (2013.01); *A61L 27/54* (2013.01); *A61L 27/56* (2013.01); *A61F 2002/2835* (2013.01); *A61F 2002/30593* (2013.01); *A61F 2002/30733* (2013.01); *A61F 2002/30787* (2013.01); *A61F 2002/30904* (2013.01); *A61F 2002/30971* (2013.01); *A61L 2300/412* (2013.01); *A61L 2430/02* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 4,437,191 A | 3/1984 | van der Zel et al. | |
| 5,681,872 A | 10/1997 | Erbe | |
| 5,700,289 A | 12/1997 | Breitbart et al. | |
| 5,776,193 A | 7/1998 | Kwan et al. | |
| 5,854,207 A | 12/1998 | Lee et al. | |
| 5,899,939 A | 5/1999 | Boyce et al. | |
| 5,914,356 A | 6/1999 | Erbe | |
| 5,939,039 A | 8/1999 | Sapieszko et al. | |
| 6,123,731 A | 9/2000 | Boyce et al. | |
| 6,264,701 B1 | 7/2001 | Brekke | |
| 6,294,041 B1 | 9/2001 | Boyce et al. | |
| 6,309,659 B1 | 10/2001 | Clokie | |
| 6,350,283 B1 | 2/2002 | Michelson | |
| 6,372,257 B1 | 4/2002 | Marchosky | |
| 6,432,436 B1 | 8/2002 | Gertzman et al. | |
| 6,437,018 B1 | 8/2002 | Gertzman et al. | |
| 6,666,890 B2 | 12/2003 | Michelson | |
| 6,696,073 B2 * | 2/2004 | Boyce ............... | A61B 17/0401 424/422 |
| 6,706,067 B2 | 3/2004 | Shimp et al. | |
| 6,723,131 B2 | 4/2004 | Muschler | |
| 6,749,636 B2 | 6/2004 | Michelson | |
| 6,752,831 B2 | 6/2004 | Sybert et al. | |
| 6,776,800 B2 | 8/2004 | Boyer, II et al. | |
| 6,808,585 B2 | 10/2004 | Boyce et al. | |
| 6,843,807 B1 | 1/2005 | Boyce et al. | |
| 6,919,308 B2 | 7/2005 | Oppermann et al. | |
| 6,949,251 B2 | 9/2005 | Dalal et al. | |
| 7,022,137 B2 | 4/2006 | Michelson | |
| 7,041,641 B2 | 5/2006 | Rueger et al. | |
| 7,132,110 B2 | 11/2006 | Kay et al. | |
| 7,156,880 B2 | 1/2007 | Evans et al. | |
| 7,166,133 B2 | 1/2007 | Evans et al. | |
| 7,175,858 B2 | 2/2007 | Constantz et al. | |
| 7,235,107 B2 | 6/2007 | Evans et al. | |

(Continued)

FOREIGN PATENT DOCUMENTS

| | | |
|---|---|---|
| CA | 1341610 C | 4/1989 |
| CA | 2027259 C | 12/2000 |

(Continued)

*Primary Examiner* — Susan T Tran

(57) ABSTRACT

Biomaterials, implants made therefrom, methods of making the biomaterial and implants, methods of promoting bone or wound healing in a mammal by administering the biomaterial or implant to the mammal, and kits that include such biomaterials, implants, or components thereof. The biomaterials may be designed to exhibit osteogenic, osteoinductive, osteoconductive, and/or osteostimulative properties.

18 Claims, 13 Drawing Sheets

(56) References Cited

U.S. PATENT DOCUMENTS

| | | |
|---|---|---|
| 7,262,003 B2 | 8/2007 | Kumar et al. |
| 7,275,933 B2 | 10/2007 | Jia et al. |
| 7,291,345 B2 | 11/2007 | Winterbottom et al. |
| 7,332,452 B2 | 2/2008 | Ogawa et al. |
| 7,390,498 B2 | 6/2008 | Dalal et al. |
| 7,393,405 B2 | 7/2008 | Bohner |
| 7,473,678 B2 | 1/2009 | Lynch |
| 7,494,950 B2 | 2/2009 | Armitage et al. |
| 7,498,041 B2 | 3/2009 | Masinaei et al. |
| 7,517,489 B2 | 4/2009 | Akash |
| 7,582,309 B2 | 9/2009 | Rosenberg et al. |
| 7,611,536 B2 | 11/2009 | Michelson |
| 7,723,395 B2 | 5/2010 | Ringeisen et al. |
| 7,744,597 B2 | 6/2010 | Gaskins et al. |
| 7,776,100 B2 | 8/2010 | Brekke et al. |
| 7,785,634 B2 | 8/2010 | Borden |
| 7,811,608 B2 | 10/2010 | Kay et al. |
| 7,824,702 B2 | 11/2010 | Wironen et al. |
| 7,833,278 B2 | 11/2010 | Evans et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,931,692 B2 | 4/2011 | Sybert et al. |
| 7,939,108 B2 | 5/2011 | Morris et al. |
| 7,942,961 B2 | 5/2011 | Asgarg |
| 7,947,759 B2 | 5/2011 | Lin et al. |
| 7,959,941 B2 | 6/2011 | Knaack et al. |
| 7,977,094 B2 | 7/2011 | Masinaei et al. |
| 8,002,813 B2 | 8/2011 | Scarborough et al. |
| 8,067,078 B1 | 11/2011 | Espinosa et al. |
| 8,093,313 B2 | 1/2012 | Miller |
| 8,105,383 B2 | 1/2012 | Michelson |
| 8,137,403 B2 | 3/2012 | Michelson |
| 8,147,860 B2 | 4/2012 | Rosenberg et al. |
| 8,147,862 B2 | 4/2012 | McKay |
| 8,163,032 B2 | 4/2012 | Evans et al. |
| 8,188,229 B2 | 5/2012 | Ringeison et al. |
| 8,197,474 B2 | 6/2012 | Scarborough et al. |
| 8,202,539 B2 | 6/2012 | Behnam et al. |
| 8,221,781 B2 | 7/2012 | Rosenberg et al. |
| 8,232,327 B2 | 7/2012 | Garigapati et al. |
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cicieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,952 B2 | 12/2012 | Nutt et al. |
| 8,343,219 B2 * | 1/2013 | Allain .............. A61B 17/0642 |
| | | 606/100 |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 2001/0018614 A1 * | 8/2001 | Bianchi .............. A61F 2/28 |
| | | 623/16.11 |
| 2001/0038848 A1 | 11/2001 | Donda et al. |
| 2002/0076429 A1 | 6/2002 | Wironen et al. |
| 2002/0098222 A1 | 7/2002 | Wironen et al. |
| 2002/0193883 A1 | 12/2002 | Wironen |
| 2003/0009235 A1 | 1/2003 | Manrique et al. |
| 2003/0039676 A1 | 2/2003 | Boyce et al. |
| 2003/0055512 A1 | 3/2003 | Genin et al. |
| 2003/0149437 A1 | 8/2003 | Livne et al. |
| 2004/0075192 A1 | 4/2004 | Boyer, II et al. |
| 2004/0091462 A1 | 5/2004 | Lin et al. |
| 2004/0243242 A1 | 12/2004 | Sybert et al. |
| 2005/0118230 A1 | 6/2005 | Hill et al. |
| 2005/0251267 A1 | 11/2005 | Winterbottom et al. |
| 2005/0281856 A1 | 12/2005 | McGlohorn et al. |
| 2006/0018942 A1 | 1/2006 | Rowe et al. |
| 2006/0036331 A1 | 2/2006 | Lu et al. |
| 2006/0046590 A1 * | 3/2006 | Chu .............. C08B 37/0072 |
| | | 442/59 |
| 2006/0147545 A1 | 7/2006 | Scarborough et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0113951 A1 | 5/2007 | Huang |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0187571 A1 | 8/2008 | Clineff et al. |
| 2008/0234822 A1 | 9/2008 | Govil |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0312842 A1 | 12/2009 | Bursac et al. |
| 2009/0317447 A1 | 12/2009 | Hsiao et al. |
| 2010/0055078 A1 | 3/2010 | Hughes-Fulford |
| 2010/0145469 A1 | 6/2010 | Barralet et al. |
| 2010/0168798 A1 * | 7/2010 | Clineff .............. A61L 27/54 |
| | | 606/279 |
| 2010/0196333 A1 | 8/2010 | Gaskins et al. |
| 2010/0203155 A1 | 8/2010 | Wei et al. |
| 2010/0234966 A1 | 9/2010 | Lo |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0224675 A1 | 9/2011 | Tofighi et al. |
| 2011/0262554 A1 | 10/2011 | Masinaei et al. |
| 2011/0276147 A1 | 11/2011 | Cook et al. |

(56) References Cited

U.S. PATENT DOCUMENTS

| | | |
|---|---|---|
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |
| 2012/0237568 A1 | 9/2012 | Murphy et al. |
| 2013/0013071 A1 | 1/2013 | Betz et al. |
| 2013/0059382 A1 | 3/2013 | Tsai et al. |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0150968 A1 | 6/2013 | Dinville et al. |
| 2013/0189338 A1 | 7/2013 | Drapeau et al. |
| 2013/0195805 A1 | 8/2013 | Wei et al. |
| 2013/0202670 A1 | 8/2013 | Darmac et al. |
| 2013/0226300 A1 | 8/2013 | Chataigner et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0031950 A1 | 1/2014 | Cook et al. |
| 2014/0079753 A1 | 3/2014 | Darby et al. |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |
| 2014/0314822 A1 | 10/2014 | Carter et al. |
| 2015/0010607 A1 | 1/2015 | Francis et al. |

FOREIGN PATENT DOCUMENTS

| | | |
|---|---|---|
| WO | 2005084701 A1 | 9/2005 |
| WO | 2006076712 A2 | 7/2006 |
| WO | 2013062716 A1 | 5/2013 |
| WO | 2014128289 A1 | 8/2014 |
| WO | 2015054547 A1 | 4/2015 |

* cited by examiner

BIOMATERIAL COMPOSITIONS, IMPLANTS, AND METHODS OF MAKING THE SAME

CROSS REFERENCE TO RELATED APPLICATION

This application is a continuation-in-part of U.S. patent application Ser. No. 14/735,460, filed Jun. 10, 2015, which is hereby incorporated by reference in its entirety for all purposes.

TECHNICAL FIELD

The present invention relates generally to bone and wound healing biomaterials. The invention relates to the biomaterials and implants formed therefrom. The invention also relates to methods of making the materials and implants, and methods of promoting bone or wound healing in a mammal by administering the biomaterial or implant to the mammal. The invention further relates to kits that include one or more of the biomaterials, implants, or components thereof.

BACKGROUND

Bone grafting is a surgical procedure that replaces missing bone and/or repairs bone fractures. Bone generally has the ability to regenerate well but may require a scaffold to do so. Bone grafts may be allograft (cadaveric bone e.g., from a bone bank), autologous (i.e., bone harvested from the patient's own body, for example from the iliac crest), or synthetic. Most bone grafts are expected to be resorbed and replaced as the natural bone heals over time.

Successful biomaterials may include osteoconduction (guiding the reparative growth of the natural bone), osteoinduction (encouraging undifferentiated cells to become active osteoblasts), and/or osteogenesis (living bone cells in the graft material contributing to bone remodeling). Although traditional bone grafts may exhibit certain advantages, traditional allograft may not exhibit the properties desired, may be difficult to obtain, or may not be in a shape or form suitable for implantation.

SUMMARY

To meet this and other needs, biomaterials described herein may be osteogenic, osteoinductive, osteoconductive, and/or osteostimulative, which may be advantageous for bone healing and repair and without the drawbacks of present allograft or autograft products. The biomaterial compositions or implants prepared therefrom can include various combinations of demineralized bone matrix (e.g., in the form of chips, fibers, or particulates), ceramics such as tricalcium phosphate, bioactive glass, and combinations thereof, a carrier such as a carrier composition containing hyaluronic acid and/or collagen, and one or more additional components each of which is described in more detail herein.

According to one embodiment, a method of making a biomaterial composition for aiding bone regeneration includes mixing a carrier with a ceramic composition including bioactive glass and calcium phosphate (e.g., beta-tricalcium phosphate) to form a biomaterial composition; adding the biomaterial composition to a mold to form a molded biomaterial composition; freeze-drying the molded biomaterial composition to form a freeze-dried composition; and crosslinking the freeze-dried composition to form a cross-linked composition. In addition, demineralized bone matrix (e.g., in the form of cortical fibers, bone chips, particulates, or the like) may be added to the biomaterial composition during the mixing step. Optionally, the method may further include crosslinking the freeze-dried composition with a chemical crosslinking agent (e.g., formaldehyde). Optionally, the method may further include sterilizing the composition, for example, with ethylene oxide and/or gamma radiation.

The biomaterial composition may also include one or more of the following attributes. The carrier may include one or more of hyaluronic acid, poloxamer, glycerol, polyethylene glycol, or the like. If hyaluronic acid is used as the carrier, for example, the hyaluronic acid may be swellable to gel form. For example, the hyaluronic acid may be mixed with water or an acid, such as hydrochloric acid, which causes the carrier to swell in volume. The bioactive glass may have a bimodal or unimodal particle size distribution. The particle size may range, for example, from about 1 to 1000 µm. The final form of the biomaterial composition may be the material itself or an implant formed therefrom. The composition or implant may be a strip, gel, putty, sponge, or the like.

According to another embodiment, a method of promoting bone or wound healing in a mammal includes providing a biomaterial composition comprising a carrier and a ceramic composition including bioactive glass and calcium phosphate (e.g., the biomaterial composition may include about 5-20% (w/w) of the carrier, about 15-20% (w/w) of the bioactive glass, and about 60-70% (w/w) of the calcium phosphate); and administering the biomaterial composition into a target repair site to facilitate repair or regeneration of bone at the target repair site. For example, the target repair site may include an injury or defect in the spine (e.g., in the cervical, thoracic, or lumbar regions).

According to another embodiment, a biomaterial composition or implant derived therefrom includes one or more of: one or more carriers, one or more ceramics, one or more demineralized bone products, and combinations thereof. By way of non-limiting example, the carrier may include a carrier composition containing hyaluronic acid and/or collagen; the ceramics may include tricalcium phosphate, bioactive glass, and combinations thereof; and the demineralized bone products may be in the form of chips, fibers, or particulates, for example, derived from cortical bone, cancellous bone, or a combination of both. The implant may be shaped, for example, in the form of a strip, ring, cylinder, plug, or the like. The implant may be used alone or in combination with a cage, frame, allograft, graft material, or other biomaterials known in the art.

According to another embodiment, a compressed and/or molded implant may include one or more of the following attributes: (1) a single piece design; (2) a multi-piece design; (3) a layered construction; (4) a solid construction; (5) provided with a central opening or multiple openings for graft material or a plug; (6) shaped with one or more notches configured to receive a portion of a bone screw; (7) a plug of the same or different material; and (8) used alone or in combination with a cage or frame, for example, to fill a central opening therein.

According to one embodiment, a method of making an implantable biomaterial for aiding bone regeneration includes obtaining demineralized bone in particulate form (e.g., powder, particles, granules, fibers, or the like derived from cortical and/or cancellous bone); adding the demineralized, particulate bone optionally mixed with bioactive glass and/or tricalcium phosphate to a mold; compressing the demineralized, particulate bone in the mold for a time and pressure sufficient to form a molded biomaterial composition of a given shape; and freeze-drying the molded biomaterial composition to form the implantable biomaterial; wherein the shape of the implantable biomaterial is determined by the mold. The implantable biomaterial may be multi-layered for example consisting of multiple layers of the particulate, demineralized bone layered together. The adjoining layers of the multi-layered implantable biomaterial may be the same or different compositionally from one another. The implantable biomaterial may include a plurality of complimentary shapes assembled together. For example, a first portion of implantable biomaterial having a mortise may be interlocked with a second portion of implantable biomaterial having a tenon received in the mortise of the first portion. In an alternative version, a plurality of substantially concentric rings may be interlocked together to form the implantable biomaterial.

According to another embodiment, a method of making a multi-layered implantable biomaterial for aiding bone regeneration includes obtaining demineralized bone in particulate form; adding a first layer of the demineralized, particulate bone to a mold; adding a second layer of the demineralized, particulate bone to the mold; optionally, adding a third layer and/or additional layers of the demineralized, particulate bone to a mold; compressing the layers of demineralized, particulate bone in the mold for a time and pressure sufficient to form a molded biomaterial composition of a given shape having separate and distinct layers; and freeze-drying the molded biomaterial composition to form the implantable biomaterial; wherein the shape of the implantable biomaterial is determined by the mold. The first and second layers may be the same or different compositionally from one another. The resulting layered implantable biomaterial may include alternating layers of different materials, for example.

According to yet another embodiment, a method of promoting bone or wound healing in a mammal includes providing a compressed, multi-layered implantable biomaterial comprised of demineralized bone in particulate form; and administering the implantable biomaterial into a target repair site to facilitate repair or regeneration of bone at the target repair site. The target repair site may include an injury or defect in the spine. The implantable biomaterial may be positioned and retained within a frame formed of a different material than the implantable biomaterial. The implantable biomaterial and the frame may form a standalone implant configured to be secured to adjacent vertebrae with one or more bone fasteners, which does not require further fixation, such as rods or plates.

According to yet another embodiment, a kit includes one or more biomaterials, implants, or components thereof described herein. For example, the kit may contain putty, gel, strip, and/or extrudable versions of the biomaterial compositions. The kit may contain biomaterial compositions of the same or different types. In addition, the kit may include other components known in the art, including, but not limited to, carriers or scaffolds, cages (e.g., titanium and/or polyether ether ketone (PEEK) spacers), allograft spacers, cell culture media, phosphate buffered saline (PBS), a tissue culture substrate, bone graft harvesting tools, bone marrow aspirate retrieval tools, or the like.

BRIEF DESCRIPTION OF THE DRAWING

The present embodiments may be more fully understood from the detailed description and the accompanying drawings in which.

DETAILED DESCRIPTION

Figure 1:
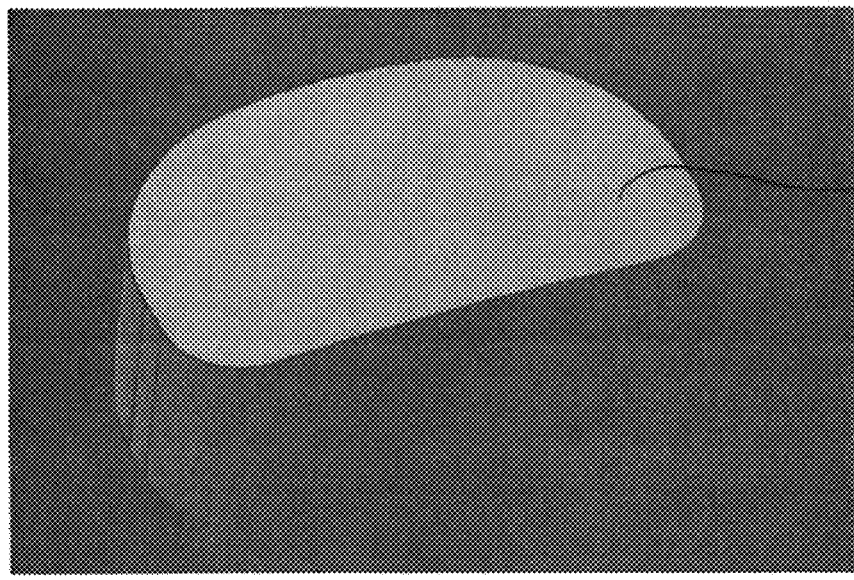
FIG. 1 depicts a compressed or molded implant having a single piece, solid construction.

The present invention relates generally to biomaterials and implants made therefrom that may exhibit osteogenic, osteoinductive, osteoconductive, and/or osteostimulative properties. The invention also relates to methods of making the biomaterial and implants, and methods of promoting bone or wound healing in a mammal by administering the biomaterial or implant to the mammal. The invention further relates to kits that include one or more of the biomaterials, implants, or components thereof.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. As used herein, unless otherwise required by context, singular terms include pluralities and plural terms include the singular.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Unless specified otherwise, all values provided herein include up to and including the endpoints given, and the values of the constituents or components of the compositions are expressed in weight percent or % by weight of each ingredient in the composition.

Each compound used herein may be discussed interchangeably with respect to its chemical formula, chemical name, abbreviation, etc. For example, PEG may be used interchangeably with polyethylene glycol.

Embodiment described herein may be generally directed to biomaterials, implants made therefrom, methods of making the same, and methods of using the same to promote healing or fusion of bone. Although biomaterials or implants may be discussed separately, it will be appreciated by one of ordinary skill in the art that the biomaterials described may be used in and of itself or may be used to create implants of different shapes, sizes, and orientations for a number of different clinical outcomes. Thus, the discussion of biomaterials may apply equally to the discussion on implants and vice versa.

The biomaterial composition may be osteogenic, osteoinductive, osteoconductive, and/or osteostimulative, which may be advantageous for bone healing and repair. The biomaterials may be osteoconductive when the material serves as a scaffold that provides surface area for new bone growth. The biomaterials may be osteoinductive if they stimulate osteoprogenitor cells or induce mesenchymal stem cells to differentiate into osteoblasts that then begin new bone formation. Biomaterials may be osteogenic if they contain cells (e.g., viable cells) that are capable of bone regeneration. The biomaterial may be osteostimulative if the material accelerates the bone formation process. The composition may also be "biocompatible" as that term refers to the ability (e.g., of a composition or material) to perform with an appropriate host response in a specific application, or at least to perform without having a toxic or otherwise deleterious effect on a biological system of the host, locally or systemically. The biomaterial and/or implant may be "biologically degradable" in that the material may be degraded by cellular absorption and/or hydrolytic degradation in a patient's body. According to some embodiments, it may be desirable that the biomaterials possess sufficient osteoconductivity, porosity, mechanical strength, and degradation times. For example, the composition may be biologically degradable over a period of time of about 3-12 months, about 3-9 months, about 3-6 months, about 6-12 months, about 6-9 months, or about 9-12 months.

According to one embodiment, the biomaterial composition may be configured to facilitate repair or regeneration of bone at a target repair site. The target repair site can be, for example, a void, gap, or other defect or surgeon created opening in a bone, between bones, or other bony structure in a body of a patient. For example, the biomaterial composition can be configured to facilitate bone growth at a target repair site in the spine, pelvis, an extremity, the cranium, or another bone, between bones, or bony structure in the patient's body. The biomaterial composition may be configured to be directly implanted or otherwise disposed at and in contact with the target repair site.

The biomaterial composition can include various combinations of demineralized bone matrix (e.g., in the form of chips, fibers, or particulates), ceramic such as calcium phosphate or bioactive glass, collagen, and one or more additional components each of which is described in more detail herein.

According to certain embodiments, the compositions may include demineralized bone matrix. Demineralized bone matrix (also known as DBM) may provide osteoconductive, osteoinductive and/or osteogenic properties. Thus, it induces the formation of bone tissue. As used herein, the terms "demineralized bone", "demineralized bone matrix", and "DBM" may be used interchangeably. The demineralized bone, for example, in the form of fibers, chips, and/or particles, can be disposed on, embedded within, and/or mixed within the biomaterial composition.

Demineralized bone matrix may be in the form of sheets, fibers, threads, strips, chips, shards, elongated particles, powder, or particulates, for example. The demineralized bone matrix may include bone pieces of all shapes, sizes, thickness, and configurations that possess regular, irregular, or random geometries. For example, fibers may have an average fiber length of about 250 µm to about 2 mm, about 250 micrometers to about 750 micrometers, about 750 micrometers to about 1.25 millimeters, or about 1.25 millimeters to about 2 millimeters. In addition, the fibers may have an aspect ratio (defined as the ratio of fiber length to diameter) of about 1:1 to about 50:1, about 10:1 to about 40:1, about 5:1 to about 10:1, or about 2:1 to about 5:1. Bone chips may have a size, for example, of about 1 mm to about 10 mm, about 1 mm to about 2 mm, about 1 mm to about 4 mm, about 1 mm to about 6 mm, about 2 mm to about 4 mm, about 2 mm to about 6 mm, about 4 mm to about 6 mm, about 6 mm to about 8 mm, or about 8 mm to about 10 mm across the largest dimension. Bone particles or particulates may range in size, for example, from about 0.01 to about 2 mm, about 0.1 mm to about 1.0 mm, about 100 to about 500 microns, or about 100 to about 400 microns. It will be appreciated that some variation in dimension is possible in the production of the demineralized bone materials.

In some embodiments, the bone used to manufacture the demineralized bone matrix can be cortical, cancellous, cortico-cancellous of autogenous, allogeneic, xenogeneic or transgeneic in origin. Thus, the fibers, chips, or particulates, for example, can include cortical, cancellous, or cortico-cancellous bone. Preferably, the demineralized bone is in the form of fibers derived from cortical bone, powder derived from cortical bone, and/or chips derived from cortico-cancellous bone.

To prepare bone matrix, the bone material is typically treated to clean, defat, sterilize, virally inactivate, disinfect, demineralize, dehydrate, and/or dry the bone matrix. Methods for preparing DBM are known to persons of ordinary skill in the art and include, but are not limited to, shaving bone into thin shavings or fibers, milling, grinding, or crushing bone into chips or particles, or the like. Before or after processing the bone, the bone material is subjected to demineralization so as to reduce inorganic content to low levels. For example, demineralized bone can be produced by acid extraction, thermal freezing, irradiation, or physical extraction of inorganic minerals from human or animal bone. In an acid extraction, inorganic acids such as hydrochloric acid or phosphoric acid, or organic acids such as formic acid, acetic acid, peracetic acid, citric acid, propionic acid, etc. may be used. As would be recognized by one of ordinary skill in the art, the amount and depth of demineralization into the bone surface can be controlled by adjusting the treatment time, temperature of the demineralizing solution, concentration of the demineralizing solution, agitation intensity during treatment, and the like.

The term "demineralized" refers to bone or bone material containing less than its original mineral content (e.g., calcium content) and may encompass "substantially demineralized," "partially demineralized," and "completely demineralized" bone material. For example, the demineralized bone may include less than 10%, less than 9%, less than 8%, less than 7%, less than 6%, less than 5%, less than 4%, less than 3%, less than 2%, or less than 1% of the original mineral content (e.g., calcium content) of the bone.

If present, the demineralized bone matrix may be included in the composition, for example, in amounts ranging from about 1-80% (w/w), 1-60% (w/w), about 10-60% (w/w), about 15-60% (w/w), about 20-60% (w/w), about 30-60% (w/w), about 10-50% (w/w), about 20-50% (w/w), about 30-50% (w/w), about 10-40% (w/w), about 20-40% (w/w), about 30-40% (w/w), about 10-35% (w/w), about 20-35% (w/w), about 30-35% (w/w), about 10-30% (w/w), about 20-30% (w/w), about 20-25% (w/w), about 50-90% (w/w), about 60-95% (w/w), about 75-99% (w/w), about 80-99% (w/w), about 90-99% (w/w), about 95-99% (w/w), or about 95-100% (w/w).

In particular, when present, the composition may include demineralize bone powder, demineralized bone chips, demineralized bone fibers or a combination thereof. For example, the demineralized bone powder may be present in amounts ranging from about 15-60% (w/w), about 15-50% (w/w), about 15-40% (w/w), about 15-30% (w/w), about 15-20% (w/w), about 20-60% (w/w), about 20-50% (w/w), about 20-40% (w/w), about 20-30% (w/w) about 30-60% (w/w), about 30-50% (w/w), about 30-40% (w/w), about 50-90% (w/w), about 60-95% (w/w), about 75-99% (w/w), about 80-99% (w/w), about 90-99% (w/w), about 95-99% (w/w), or about 95-100% (w/w). For example, demineralized bone chips may be present in amounts ranging from about 1-20% (w/w), about 5-20% (w/w), about 10-20% (w/w), about 15-20% (w/w), 1-15% (w/w), about 5-15% (w/w), about 10-15% (w/w), 1-10% (w/w), about 5-10% (w/w), or 1-5% (w/w). For example, the demineralized bone fibers may be present in amounts ranging from 15-60% (w/w), about 15-50% (w/w), about 15-40% (w/w), about 15-30% (w/w), about 15-20% (w/w), about 20-60% (w/w), about 20-50% (w/w), about 20-40% (w/w), about 20-30% (w/w) about 30-60% (w/w), about 30-50% (w/w), about 30-40% (w/w), about 50-90% (w/w), about 60-95% (w/w), about 75-99% (w/w), about 80-99% (w/w), about 90-99% (w/w), about 95-99% (w/w), or about 95-100% (w/w).

According to certain embodiments, the compositions may include a ceramic component. For example, the ceramic may include ceramic mineral or inorganic filler useful for promoting bone formation. The ceramic component may include, but is not limited to, synthetic and naturally occurring inorganic fillers such as alpha-tricalcium phosphate, beta-tricalcium phosphate, tetra-tricalcium phosphate, dicalcium phosphate, calcium carbonate, barium carbonate, calcium sulfate, barium sulfate, hydroxyapatite (HA), biphasic calcium phosphate (e.g., composite between HA and β-TCP), bioactive glass, and combinations and mixtures thereof. Tricalcium phosphate and bioactive glass share similar surface properties and show enhanced osteoconductivity in in vivo settings. Tricalcium phosphate has a similar composition to hydroxyapatite, but resorbs faster due to a lower calcium to phosphate (Ca/P) ratio. For example, hydroxyapatite has a Ca/P ratio of about 1.67 whereas tricalcium phosphate has a Ca/P ratio of about 1.5.

If present, one or more ceramics may be included in the composition depending on the type or types of ceramic present, for example, in amounts ranging from about 10-40% (w/w), about 10-30% (w/w), about 10-20% (w/w), about 25-35% (w/w), about 20-40% (w/w), about 20-30% (w/w), about 15-40% (w/w), about 15-30% (w/w), or about 15-20% (w/w), about 40-70% (w/w), about 40-80% (w/w), about 50-70% (w/w), about 50-80% (w/w), about 60-70% (w/w), about 60-80% (w/w), or about 65-70% (w/w), 50-95% (w/w), about 60-95% (w/w), about 70-95% (w/w), about 75-95% (w/w), about 50-90% (w/w), about 60-90% (w/w), about 70-90% (w/w), about 75-90% (w/w), about 80-90% (w/w), or about 85-90% (w/w).

In certain embodiments, the ceramic comprises beta-tricalcium phosphate (TCP). The calcium phosphate may be configured to facilitate regrowth of bone at the target repair site. In some embodiments, the calcium phosphate of the bone graft composition is an osteoinductive agent. The calcium phosphate is configured to be disposed on, embedded in, or otherwise mixed within the biomaterial composition. The calcium phosphate can be in any suitable form. For example, the calcium phosphate can be in particulate or granular form. The calcium phosphate may have a particle size ranging from about 1 to 500 μm, about 25 to about 450 μm, about 50 to about 400 μm, about 75 to about 300 μm, or about 100 to about 250 μm. The calcium phosphate may be porous or non-porous. Preferably, the calcium phosphate is a non-porous tricalcium phosphate.

If present, tricalcium phosphate may be included in the composition, for example, in amounts ranging from about 40-70% (w/w), about 40-80% (w/w), about 50-70% (w/w), about 50-80% (w/w), about 60-70% (w/w), about 60-80% (w/w), or about 65-70% (w/w).

The ceramic may also comprise a bioactive glass. The bioactive glass may also be configured to facilitate the regrowth of bone at the target repair site. In some embodiments, the bioactive glass can be an osteoconductive agent. Bioactive glass possesses osteostimulative properties, which may be useful in the regeneration of hard tissues. The bioactive glass can be disposed on, embedded within, and or mixed within the biomaterial composition. The bioactive glass can be any alkali-containing ceramic, glass, glass-ceramic, or crystalline material that facilitates bone formation after contact with a biological environment. Suitable bioactive glasses include sol gel derived bioactive glass, melt derived bioactive glass, silica based bioactive glass, silica free bioactive glass such as borate based bioactive glass and phosphate based bioactive glass, crystallized bioactive glass (either partially or wholly), and bioactive glass containing trace elements or metals such as copper, zinc, strontium, magnesium, zinc, fluoride, mineralogical calcium sources, and the like.

Exemplary bioactive glass can include bioglass 4555 (46.1 mol % $SiO_2$, 26.9 mol % CaO, 24.4 mol % $Na_2O$ and 2.5 mol % $P_2O_5$), 58S (60 mol % $SiO_2$, 36 mol % CaO and 4 mol % $P_2O_5$), 70S30C (70 mol % $SiO_2$, 30 mol % CaO), or a combination of the foregoing bioglass. The bioactive glass may take the form of fibers, granules, particles, or a combination thereof. The bioactive glass may be irregular in shape, for example. The bioactive glass may have a unimodal or bimodal particle size distribution. The bioactive glass may have a particle size, for example, ranging from about 1 to 1000 µm, about 50 to 750 µm, or about 75 to 500 µm. Particle size and distribution may be determined by routine techniques known in the art including sieve analysis or BET (Brunauer, Emmett and Teller) testing, for example.

If present, bioactive glass may be included in the composition, for example, in amounts ranging from about 10-40% (w/w), about 10-30% (w/w), about 10-20% (w/w), about 25-35% (w/w), about 20-40% (w/w), about 20-30% (w/w), about 15-40% (w/w), about 15-30% (w/w), or about 15-20% (w/w).

According to certain embodiments, the compositions may include collagen. The collagen may have osteoconductive properties, for example, to function as a scaffold at the target repair site. The collagen can be or include soluble collagen, insoluble collagen, or a combination thereof. The collagen can be or include type I collagen, type II collagen, type III collagen, type VII collagen, another suitable type of collagen, or a combination thereof. The collagen can be derived from human, equine, bovine, porcine, murine, synthetic, or from another suitable source. In one embodiment, the collagen is of mammalian origin, preferably human. The collagen may be in particulate, gel, or another suitable form. The collagen may be porous or non-porous.

If present, collagen may be included in the composition, for example, in amounts ranging from about 1-20% (w/w), about 1-15% (w/w), about 1-10% (w/w), about 1-5% (w/w), about 5-20% (w/w), about 5-15% (w/w), about 5-10% (w/w), about 8-20% (w/w), about 8-15% (w/w), or about 8-10% (w/w).

In addition to or in place of collagen, one or more carrier, scaffold materials, or processing additives may be used in the biomaterial composition. The carrier may affect the overall handling of the material and can influence the safety, efficacy, and functionality of the material (e.g., osteoinductivity). Preferably, the carrier is inert or enhances osteogenic, osteoinductive, osteoconductive, and/or osteostimulative properties of the composition. Suitable carriers, scaffolds, or additives may include, but are not limited to, phospholipids, carboxylmethylcellulose (CMC), glycerin, glycerol, polyethylene glycol (PEG), hydrogels, poloxamers, polylactic acid (PLA), polylactic-co-glycolic acid (PLGA), other copolymers of the same family, and combinations thereof.

By way of example, the carrier may include a hydrogel, including a reverse phase hydrogel or temperature sensitive hydrogel, such as a poloxamer (e.g., a PEO-PPO-PEO triblock copolymer). In particular, the poloxamer may include poloxamer 407, poloxamer P188, poloxamer P338, or the like. The poloxamer may also be chemically modified, for example, where one or more of the terminal hydroxyl groups are replaced with methoxy groups. Other suitable materials may include hyaluronic acid (HA), sodium alginate, saline or bone marrow aspirate, for instance. The carrier, scaffold materials, or processing additives may be either water-based or non-water based.

If present, one or more carriers may be included in the composition, depending on the type or types of carrier in amounts ranging from, for example, about 1-20% (w/w), about 1-15% (w/w), about 1-10% (w/w), about 1-5% (w/w), about 5-20% (w/w), about 5-15% (w/w), about 5-10% (w/w), about 8-20% (w/w), about 8-15% (w/w), or about 8-10% (w/w), about 10-40% (w/w), about 10-30% (w/w), about 10-20% (w/w), about 25-35% (w/w), about 20-80% (w/w), about 20-70% (w/w), about 20-60% (w/w), about 20-50% (w/w), about 20-40% (w/w), about 20-30% (w/w), about 15-40% (w/w), about 15-30% (w/w), or about 15-20% (w/w), about 40-70% (w/w), about 40-80% (w/w), about 50-70% (w/w), about 50-80% (w/w), about 60-70% (w/w), about 60-80% (w/w), or about 65-70% (w/w), 50-95% (w/w), about 60-95% (w/w), about 70-95% (w/w), about 75-95% (w/w), about 50-90% (w/w), about 60-90% (w/w), about 70-90% (w/w), about 75-90% (w/w), about 80-90% (w/w), or about 85-90% (w/w).

In the case of a hydrogel, such as a poloxamer, hyaluronic acid or alginate, the materials may be swellable in volume. For example, the carrier (e.g., HA) may be mixed with water, a buffer, or an acid, such as hydrochloric acid, nitric acid, sulfuric acid, or the like, which causes the carrier to swell in volume. In an exemplary embodiment, hyaluronic acid is swellable in volume when immersed in hydrochloric acid. As will be recognized by one of ordinary skill in the art, swelling of the hydrogel may be influenced by a number of factors, such as temperature, surface area, molecular weight, degree of crosslinking, pH, or the like. By way of example, the carrier may be swellable at a reduced temperature, for example, in the range of about 1-15° C., about 1-10° C., about 1-6° C., about 2-4° C., about 2-5° C., about 2-6° C., about 3-6° C., or about 3-5° C.

If present, hyaluronic acid may be included in the composition, for example, in amounts ranging from about 0.1-5% (w/w), about 0.1-2% (w/w), about 1-5% (w/w), about 1-4% (w/w), about 1-3% (w/w), about 1-2% (w/w), or about 2% (w/w).

If present, poloxamer may be included in the composition, for example, as a hydrogel comprised of a mixture of poloxamer and water in amounts ranging from about 10-50% poloxamer, about 10-40% poloxamer, about 10-30% poloxamer, about 20-50% poloxamer, about 20-40% poloxamer, about 20-30% poloxamer, about 30-50% poloxamer, about 30-40% poloxamer with the remainder being water. The hydrogel mixture may be present in the final composition, for example, in amounts ranging from about 50-90% (w/w), about 50-80% (w/w), about 50-75% (w/w), about 60-90% (w/w), about 60-80% (w/w), about 60-75% (w/w), about 65-80% (w/w), about 65-75% (w/w), about 60-80% (w/w), or about 60-75% (w/w).

Additionally, biological agents may be added to the biomaterial or implant. These biological agents may comprise bone morphogenic protein (BMP), a peptide, a bone growth factor such as platelet derived growth factor (PDGF), vascular endothelial growth factor (VEGF), insulin derived growth factor (IDGF), a keratinocyte derived growth factor (KDGF), or a fibroblast derived growth factor (FDGF), stem cells, bone marrow, and platelet rich plasma (PRP), to name a few. If desired, one or more active pharmaceutical ingredients or medicaments may be incorporated into the biomaterial or implant as well. Biological agents may be added in any suitable pharmaceutically acceptable and effective amounts known in the art.

According to one embodiment, the composition includes a scaffold containing TCP and bioactive glass to aid in bone regeneration. In particular, a bioactive ceramic scaffold may be produced by combining tricalcium phosphate and bioactive glass. In addition, the bioactive scaffold containing tricalcium phosphate and bioactive glass may optionally be mixed with one or more of bovine type I collagen, hyaluronic acid, glycerol, and/or polyethylene glycol to facilitate handling properties. These biomaterials may possess sufficient osteoconductivity, porosity, mechanical strength, and degradation times for the intended application.

According to a particular embodiment, the composition includes a bioactive scaffold including about 50-65% (w/w) tricalcium phosphate and about 20-35% (w/w) bioactive glass. In addition, the bioactive scaffold may include about 4-12% (w/w) collagen and about 1-3% (w/w) hyaluronic acid. According to another embodiment, the composition includes a bioactive scaffold including about 60-70% (w/w) tricalcium phosphate and about 15-30% (w/w) bioactive glass. In addition, the bioactive scaffold may include about 8-15% (w/w) collagen and about 0.1-2% (w/w) hyaluronic acid.

According to another embodiment, the composition includes a scaffold containing demineralized cortical fibers, demineralized bone powder, TCP, and bioactive glass to aid in bone regeneration. In addition, the bioactive scaffold may optionally be mixed with one or more of hyaluronic acid, poloxamer, glycerol, and/or polyethylene glycol to facilitate handling.

According to yet another embodiment, the composition includes demineralized bone powder and a hydrogel. For example, the composition may include demineralized bone powder, poloxamer, water, and optionally demineralized bone chips. In particular, the composition may include about 15-60% (w/w) of demineralized bone powder and about 40-85% (w/w) carrier including about 15-40% (w/w) poloxamer with the remainder water. According to another embodiment, the composition includes about 20-40% (w/w) of demineralized bone powder, up to 20% (w/w) demineralized bone chips, and about 60-80% (w/w) carrier including about 30-40% (w/w) poloxamer with the remainder water.

The biomaterial composition may be obtained using any suitable procedures and techniques known in the art. For example, components of the composition described herein may be mixed together to form the resulting composition. The components may be combined under agitation, for example, at room temperature (e.g., about 20 and 26° C.), an elevated or reduced temperature, or any other suitable temperature and conditions known in the art.

The biomaterial composition may be added to a mold to form a molded biomaterial composition. The form or mold may be of any suitable size and shape to obtain the desired shaped implant or a portion thereof. In particular, the mold may be provided under a given pressure and temperature necessary to form a compressed implant. In other words, the composition may be compressed for a time and pressure sufficient to create the desired shaped implant or a portion thereof. The pressure exerted upon the biomaterial composition may cause the demineralized bone particles and/or other components to contact one another and adhere together. Preferably, the mold is provided under an elevated pressure (i.e., greater than atmospheric) sufficient to compress the biomaterial into a solid form. The biomaterial or resulting implant may be formed, for example, in the shape of putty, gel, paste, strip, sheet, morsels, sponge, crunch, extrudable or flowable material (e.g., from a syringe), or the like. In addition, a pattern or design may be cut into or from the molded implant to form other desired shapes.

Exemplary pressures for molding may include pressures ranging from about 15 psi to about 30,000 psi, about 15 psi to about 10,000 psi, about 15 psi to about 1000 psi, about 15 psi to about 500 psi, about 15 psi to about 100 psi, about 15 psi to about 50 psi, about 15 psi to about 25 psi, about 15 psi to about 20 psi, about 20 psi to about 20,000 psi, about 20 psi to about 10,000 psi, about 20 psi to about 1000 psi, about 20 psi to about 500 psi, about 20 psi to about 100 psi, about 20 psi to about 20 psi, about 20 psi to about 25 psi, about 30 psi to about 10,000 psi, about 30 psi to about 1000 psi, about 30 psi to about 500 psi, about 30 psi to about 100 psi, about 30 psi to about 50 psi, about 40 psi to about 5000 psi, about 40 psi to about 1000 psi, about 40 psi to about 500 psi, about 40 psi to about 100 psi, about 40 psi to about 50 psi, about 50 psi to about 2500 psi, about 50 psi to about 1000 psi, about 50 psi to about 500 psi, about 50 psi to about 100 psi, about 100 psi to about 1000 psi, about 100 psi to about 500 psi, or about 100 psi to about 200 psi. The particular pressure to be used may depend on the materials being pressed together.

Exemplary times for compressing the composition may include times ranging from about 1 to 200 minutes, about 1 to 100 minutes, about 1 to 50 minutes, about 1 to 25 minutes, about 1 to 10 minutes, about 1 to 5 minutes, 5 to 200 minutes, about 5 to 100 minutes, about 5 to 50 minutes, about 5 to 25 minutes, about 5 to 10 minutes, 10 to 200 minutes, about 10 to 100 minutes, about 10 to 50 minutes, about 10 to 25 minutes, 15 to 200 minutes, about 15 to 100 minutes, about 15 to 50 minutes, or about 15 to 25 minutes. The particular time used may depend on the materials being pressed together.

The biomaterial composition may be compressed in the mold at about room temperature or at an elevated temperature. For example, the composition may be compressed at a temperature in the range of about 20 to 100° C., about 20 to 50° C., about 20 to 40° C., about 20 to 30° C., about 20 to 25° C., about 25 to 50° C., about 25 to 40° C., about 25 to 30° C., about 30 to 50° C., or about 30 to 40° C. The particular temperature used may depend on the materials being pressed together.

The resulting material may be solid, layered, non-porous, porous, sponge-like, or of any other suitable configuration. For example, it may be desirable that the resulting biomaterial or implant is substantially non-porous. In an alternative embodiment, the resulting biomaterial or implant may be partially or completely porous (e.g., having a porosity). For example, the average pore size may range from about 1-1000 microns, about 50-750 microns, or about 200-500 microns. Pore size may be determined by routine techniques known in the art including measurements via $N_2$ adsorption, BET (Brunauer, Emmett and Teller) testing, for example.

The compositions may be sterilized, for example, by subjecting the material to chemical and/or radiation sterilization. For example, chemical sterilization may include exposure to a chemical sterilizing agent, such as ethylene oxide, nitrogen dioxide, ozone, or the like. Radiation sterilization may include exposing the material to a sterilizing source such as gamma, x-ray, and/or electron irradiation. The composition may be dehydrated or dried, for example, by air or by freeze-drying. Freeze-drying may include freezing the material (e.g., in liquid nitrogen) and reducing the surrounding pressure to allow the frozen water in the material to sublimate directly from the solid phase to the gas phase. In addition, the composition may be partially of fully crosslinked. For example, crosslinking may occur by exposing the material to a chemical crosslinking agent including mono aldehydes such as formaldehyde, acetaldehyde, or glutaraldehyde. In addition or in the alternative, crosslinking may occur by exposing the material to a crosslinking source, such as gamma, ultraviolet, or thermal sources.

In addition, the biomaterial may be formed into a specific size and shape for a desired application. For example, the implant may have a footprint suitable for cervical, thoracic, or lumbar applications. The implant may be shaped, for example, in the form of a strip, ring, cylinder, plug, or the like. The implant may be provided with one or more openings or windows suitable to be filled with the biomaterials described herein or other graft materials known in the art. The implant may be used alone or in combination with a cage, frame, allograft, graft material, or other biomaterials known in the art. The implants may be suitable for an anterior, posterior, lateral, oblique, anterolateral, transforaminal approach, or other suitable approach known in the art.

According to one embodiment, an implant is made from a particulate, demineralized bone tissue that is loaded into a mold, compressed, and freeze-dried. The shape of the final implant is determined by a mold shape rather than a pattern cut, and optionally assembled from, solid bone tissue.

According to another embodiment, an implant is made from particulate, demineralized bone tissue that is loaded into a mold, compressed, and optionally freeze-dried. The shape of the final implant or portions of the implant to be assembled together are determined by the mold shape. The final compressed implant may be used alone or in combination with a solid bone allograft and/or a cage or frame, for example, made from an implant grade material such as titanium or polyether ether ketone (PEEK).

The compressed and/or molded implant may include, for example, one or more of the following attributes: (1) a single piece design; (2) a multi-piece design; (3) a layered construction; (4) a solid construction; (5) provided with a central opening or multiple openings for graft material; (6) shaped with one or more notches configured to receive a portion of a bone screw; (7) a plug of the same or different material; and (8) used alone or in combination with a cage or frame, for example, to fill a central opening therein.

Figure 2:
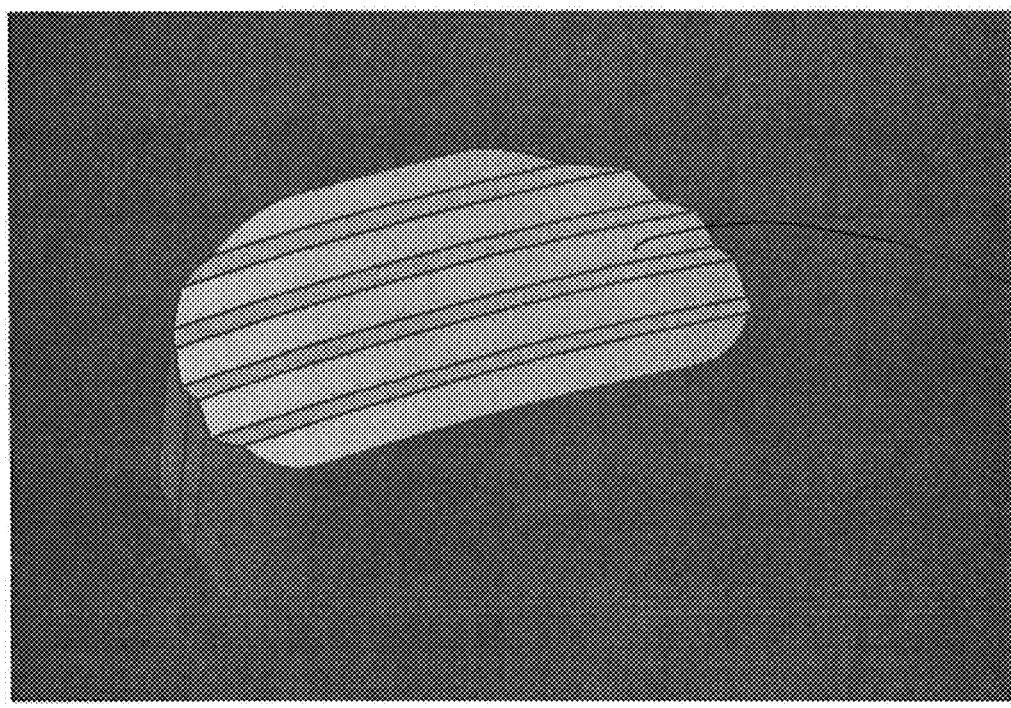
FIG. 2 depicts a compressed or molded implant having a single piece, solid construction having a plurality of ridges and grooves on the vertebral engaging surfaces.

Turning now to FIGS. 1-19, various embodiments utilizing compressed demineralized bone compositions are shown. FIG. 1 depicts a compressed and/or molded implant 10 having a single piece, solid construction. In other words, a single mold is used to form the implant 10 from the demineralized bone composition. The implant 10 or any other implant described herein may have various shapes, such as round, square, rectangular, banana-shaped, kidney-shaped, or other similar shapes. The resulting implant 10 may be molded to have substantially rounded and/or planar side walls. As shown in FIG. 1, the top and bottom, bone engaging surfaces may be substantially flat or planar. It is also envisioned that the top and bottom, bone engaging surfaces may be curved, angled, or the like to better fit the anatomy of the adjacent vertebrae. Alternatively, the bone engaging surface may include protrusions, teeth, or the like. FIG. 2 depicts a compressed or molded implant 12 having a single piece, solid construction with a plurality of ridges and grooves on the vertebral engaging surfaces.

Figure 3:
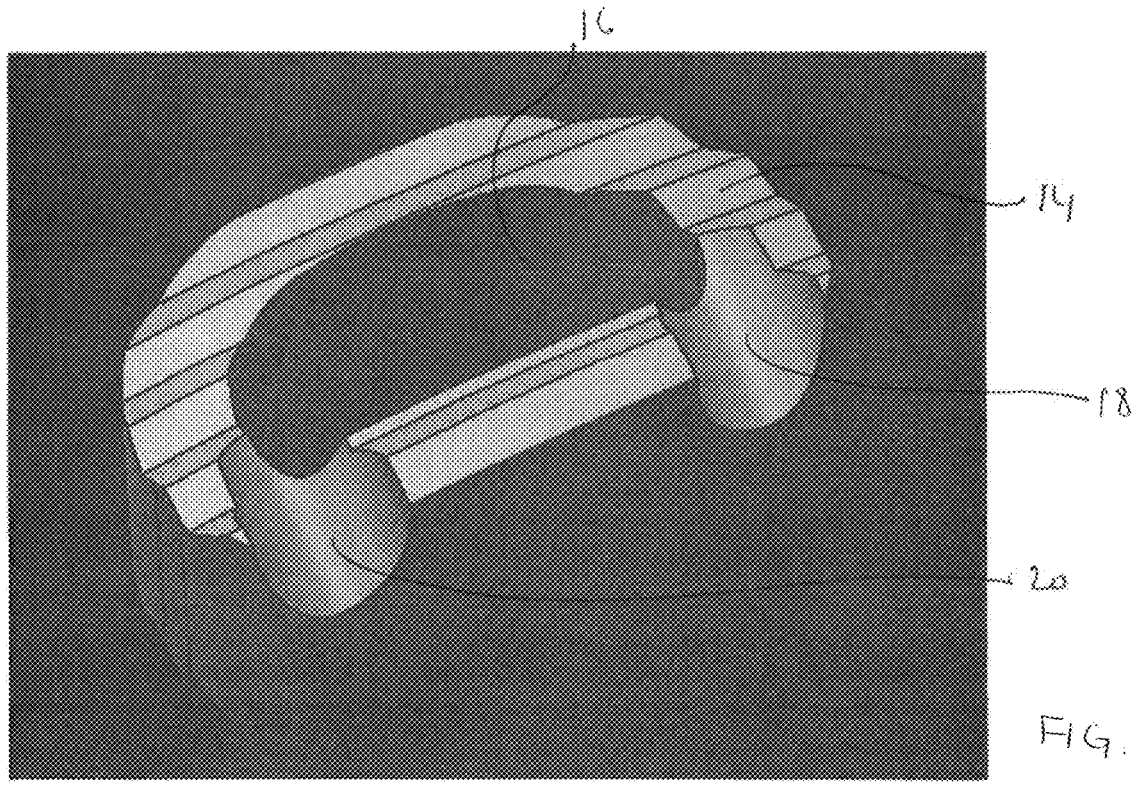
FIG. 3 is a compressed or molded implant having a single piece, solid construction with a central opening configured to retain bone graft material and notches each configured to receive a portion of a bone screw.

The implants may be provided with one or more openings, for example, to receive one or more bone graft materials to promote fusion to the adjacent vertebral bodies. For example, cadaveric bone, autologous bone, bone slurry, bone morphogenic protein (BMP), or other similar materials, may enhance tissue growth within the intervertebral space. FIG. 3 shows a compressed or molded implant 14 having a single piece, solid construction with a single central opening 16. The opening 16 may extend from a first bone engaging surface to a second bone engaging surface to define a substantially hollow center suitable for retaining one or more of the bone graft materials. The bone engaging surfaces may include ridges and/or grooves as shown.

The implants may be provided with one or more notches, for example, each configured to receive a portion of a fastening element or fastener such that the implants or a portion thereof may be provided as a standalone device, for example, without the need for additional fixation by plates, rods, additional fasteners, or the like. The fastening elements may include bone screws, pins, nails, spikes, or the like. FIG. 3 shows a compressed or molded implant 14 having first and second notches 18, 20 configured to receive a portion of first and second fasteners (not shown).

Figure 4:
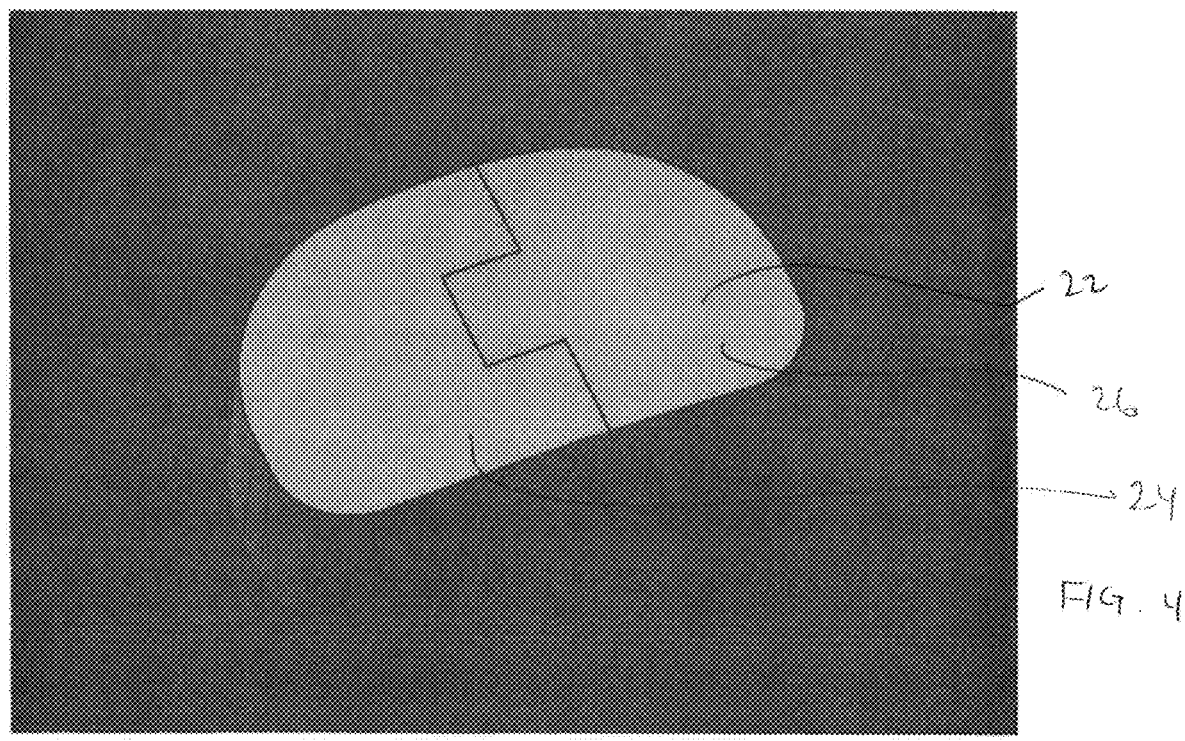
FIG. 4 depicts a compressed or molded implant having a multi-piece, solid construction where the components are interlocked together.
Figure 5:
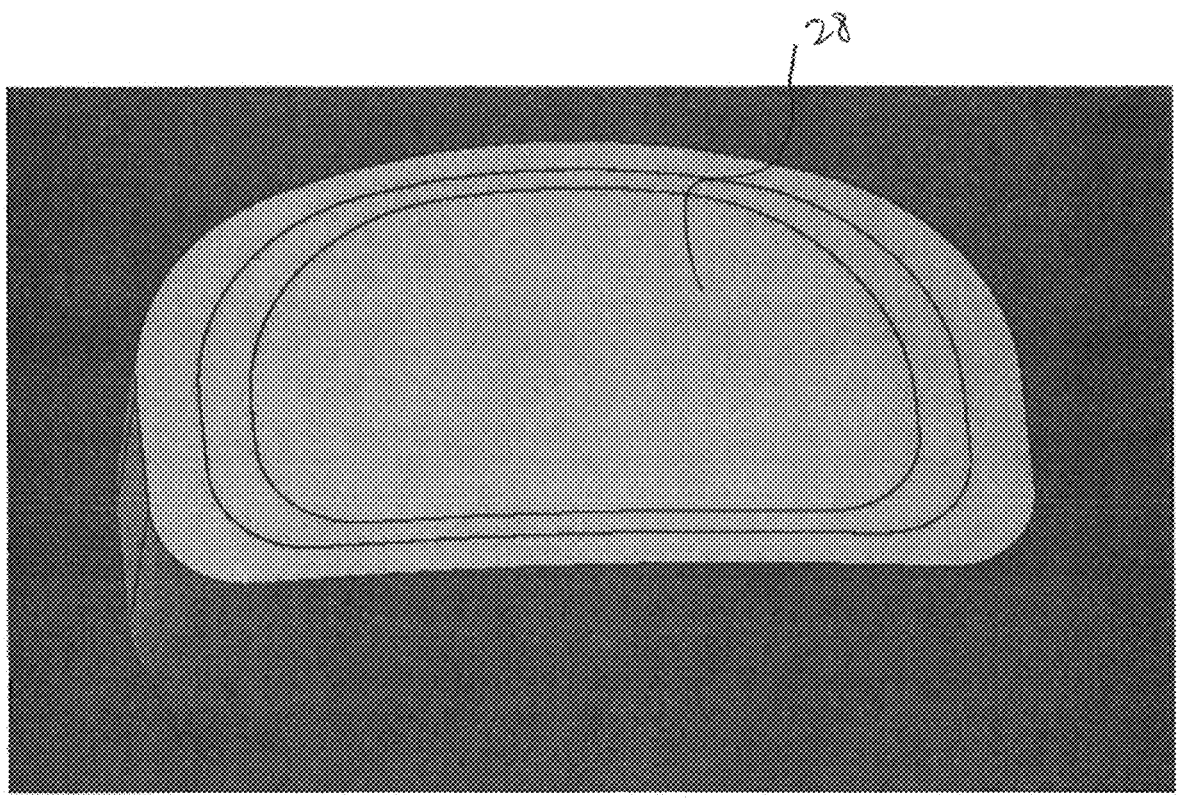
FIG. 5 is a compressed or molded implant having a multi-piece, solid construction where concentric rings of the compressed or molded material are joined together.

The implants may be formed from a multi-piece design and assembled using techniques typically employed with solid bone. For example, two or more pieces may be assembled together, for example, using mortise and tenon joints, dovetail connections, tongue and groove, pins, shims, adhesive, or other similar mechanisms for joining multiple pieces of material together. FIG. 4 depicts a compressed or molded implant 22 having a multi-piece, solid construction where the components are interlocked together. In particular, a first portion 24 having a recess or mortise may be interlocked with a second portion 26 having an extension or tenon, which is received in the recess or mortise of the first portion 24. FIG. 5 shows a compressed or molded implant 28 having a multi-piece, solid construction where multiple substantially concentric rings of the compressed or molded material are joined together. The concentric rings may have the same or varying thicknesses.

The compressed implant material may be combined with a frame or cage to create the final implantable device, such as a standalone implant. In particular, the frame or cage may have a central opening sized and dimensioned to receive the compressed and/or molded implant. The frame or cage may be of any suitable shape or design and may include attributes, such as a bone engaging surfaces with protrusions, teeth, ridges and grooves, or the like, or areas to engage an insertion instrument or the like, for example. The cage may also include one or more openings designed to receive a portion of one or more fasteners (not shown), such as bone screws, to secure the implant to one or both of the adjacent vertebrae.

Figure 6:
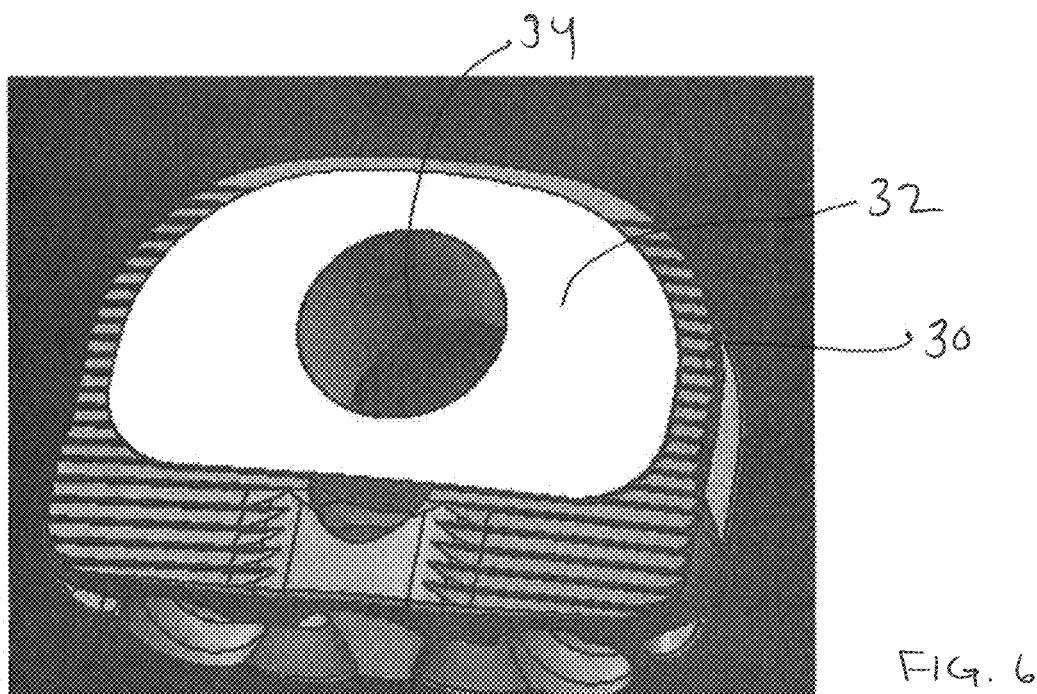
FIG. 6 shows a frame or cage retaining a compressed or molded implant in solid form having an opening configured to receive a plug of bone graft material.
Figure 11:
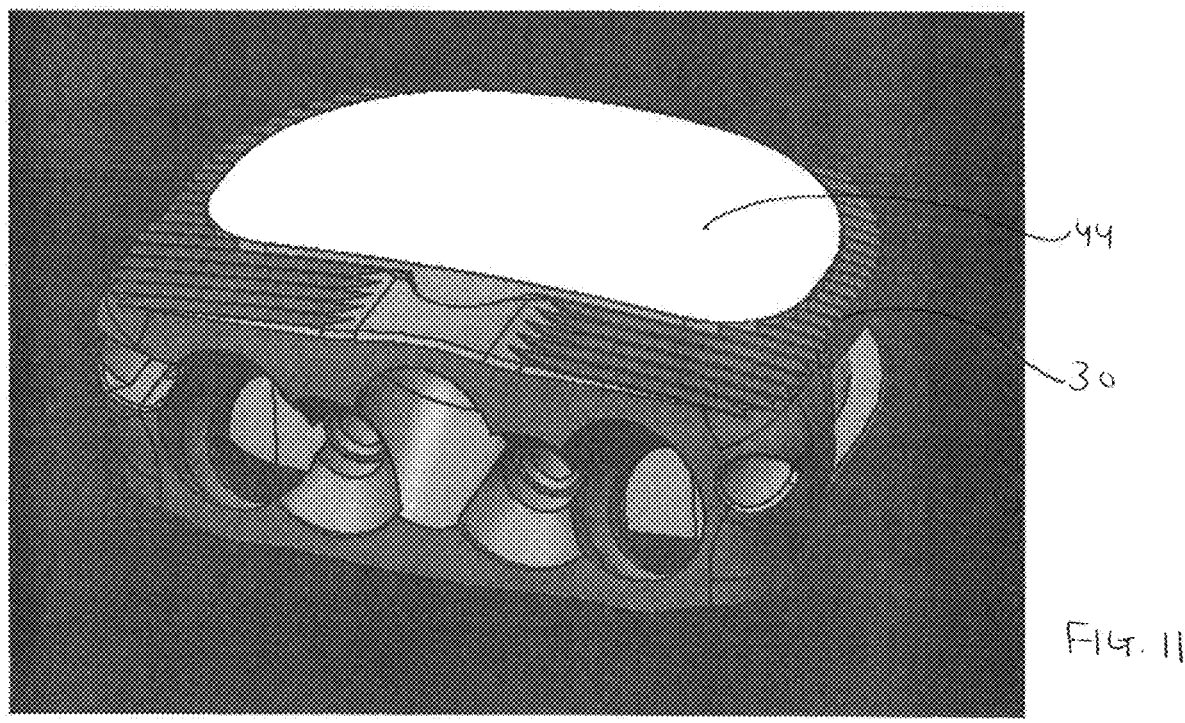
FIG. 11 shows the frame or cage depicted in FIG. 6 where the compressed or molded implant has a single piece construction in solid form.
Figure 12:
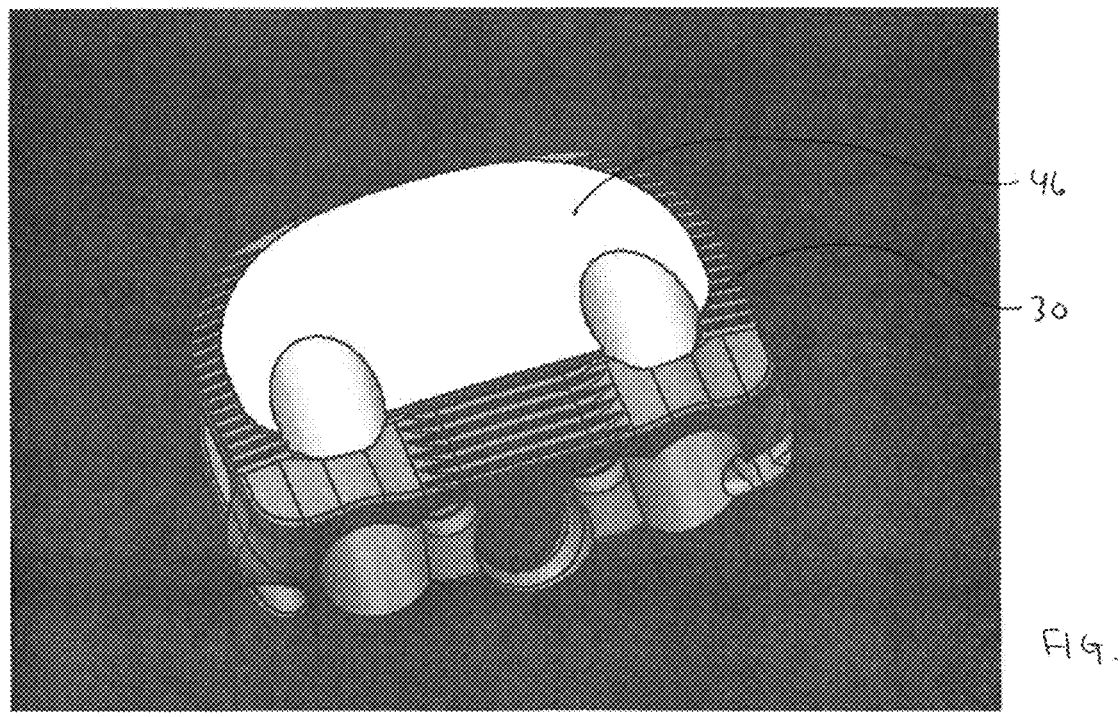
FIG. 12 is the frame or cage depicted in FIG. 6 where the solid compressed or molded implant includes multiple notches each configured to receive a portion of a bone screw.
Figure 13:
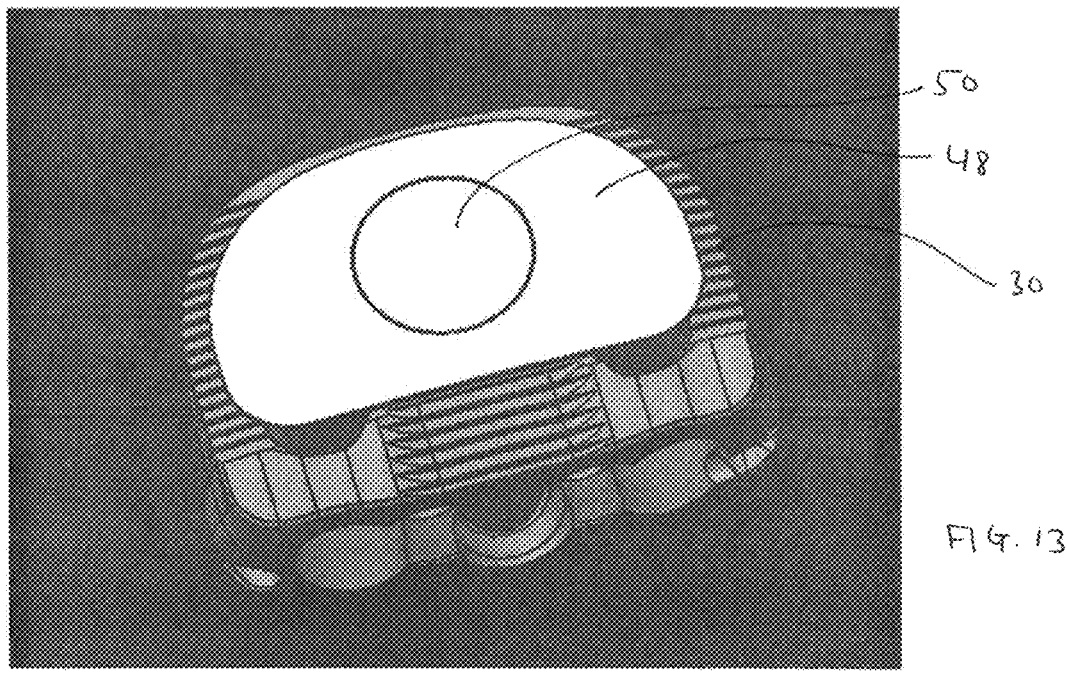
FIG. 13 is the frame or cage depicted in FIG. 6 where the solid compressed or molded has an opening with a plug of bone graft material received therein.
Figure 14:
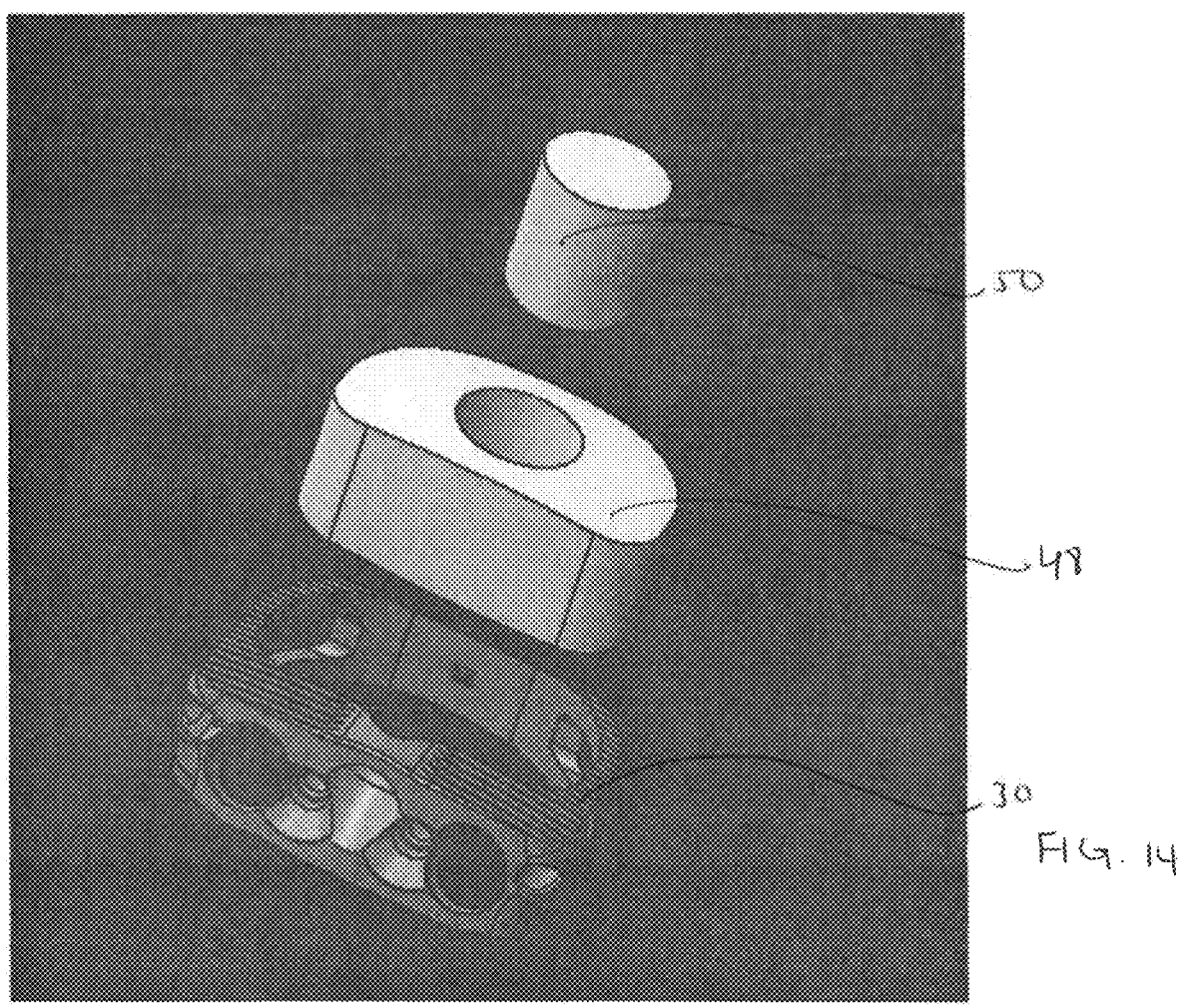
FIG. 14 shows the embodiment depicted in FIG. 13 in an exploded view.
Figure 15:
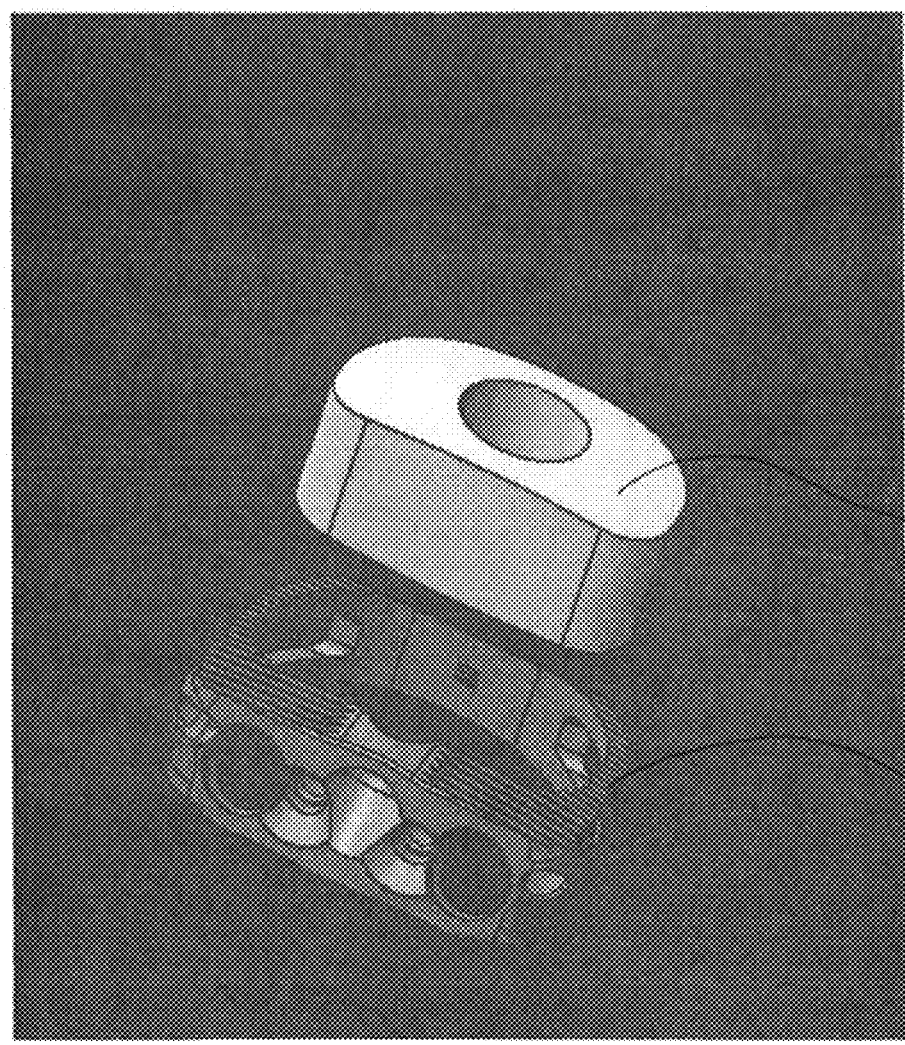
FIG. 15 shows the embodiment depicted in FIG. 13 in an exploded view with the plug removed.
Figure 16:
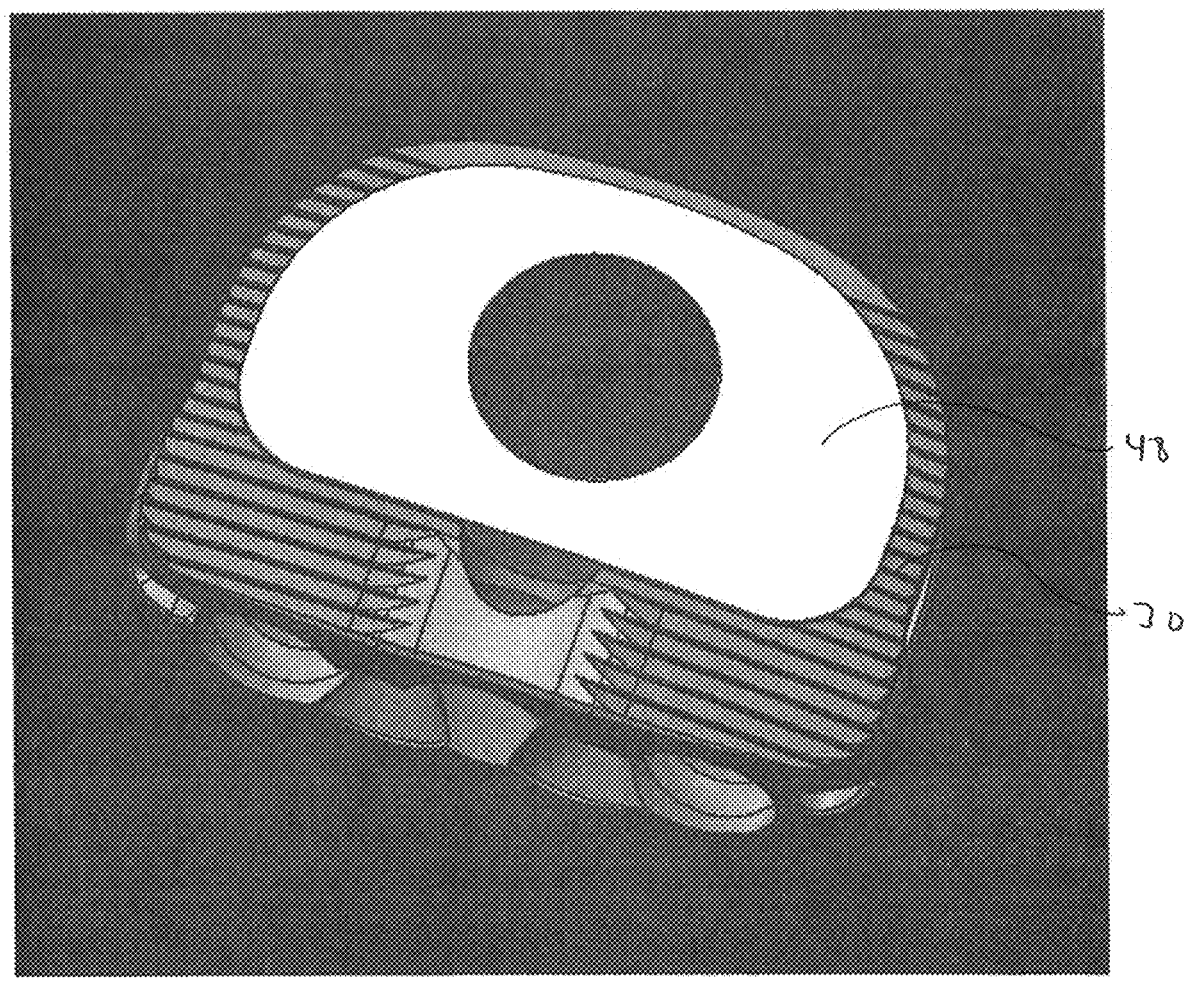
FIG. 16 shows the embodiment depicted in FIG. 13 with the plug removed.
Figure 18:
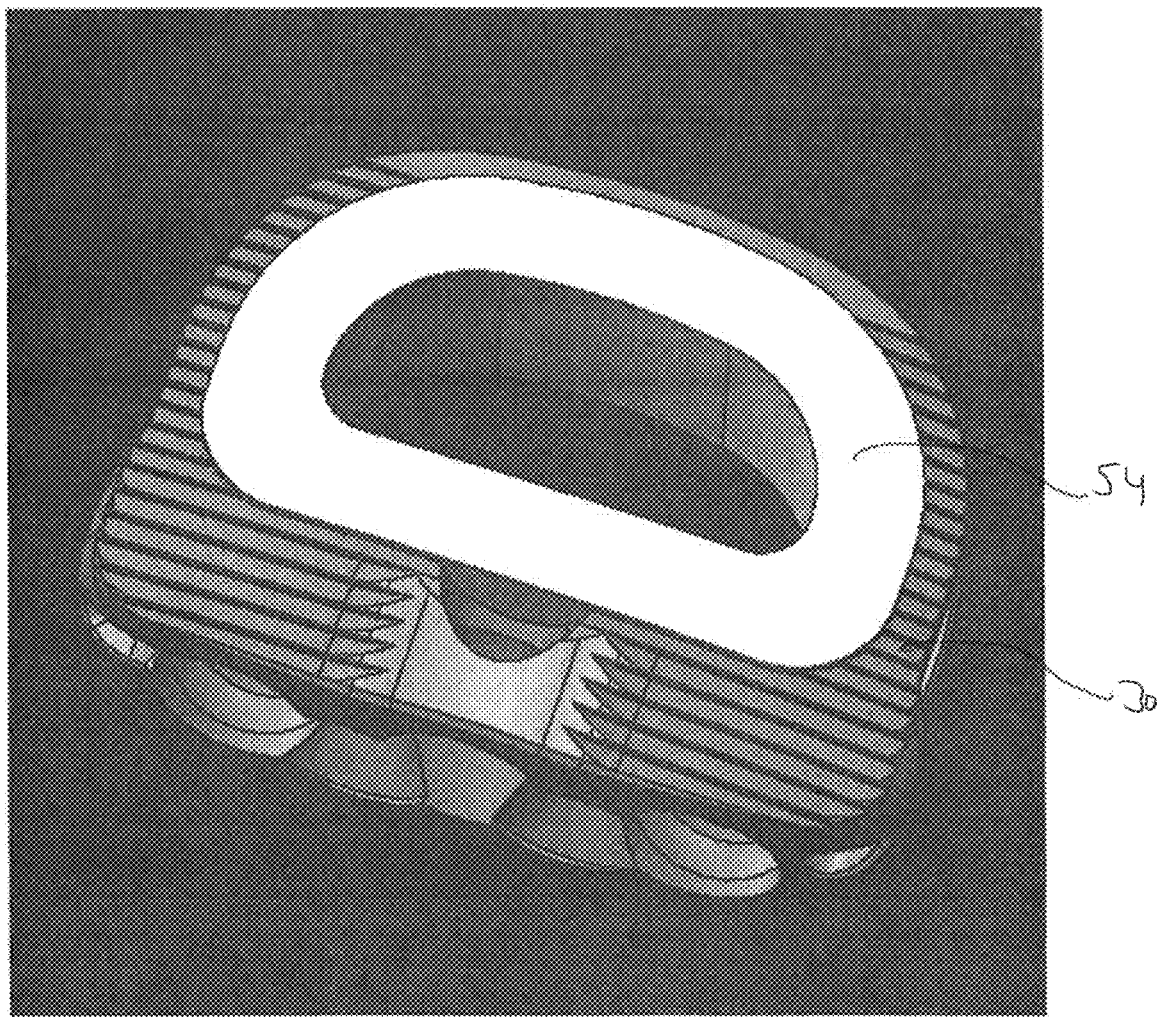
FIG. 18 depicts the frame or cage depicted in FIG. 6 where the compressed or molded implant has a solid construction with an elongated opening configured to receive bone graft materials.
Figure 19:
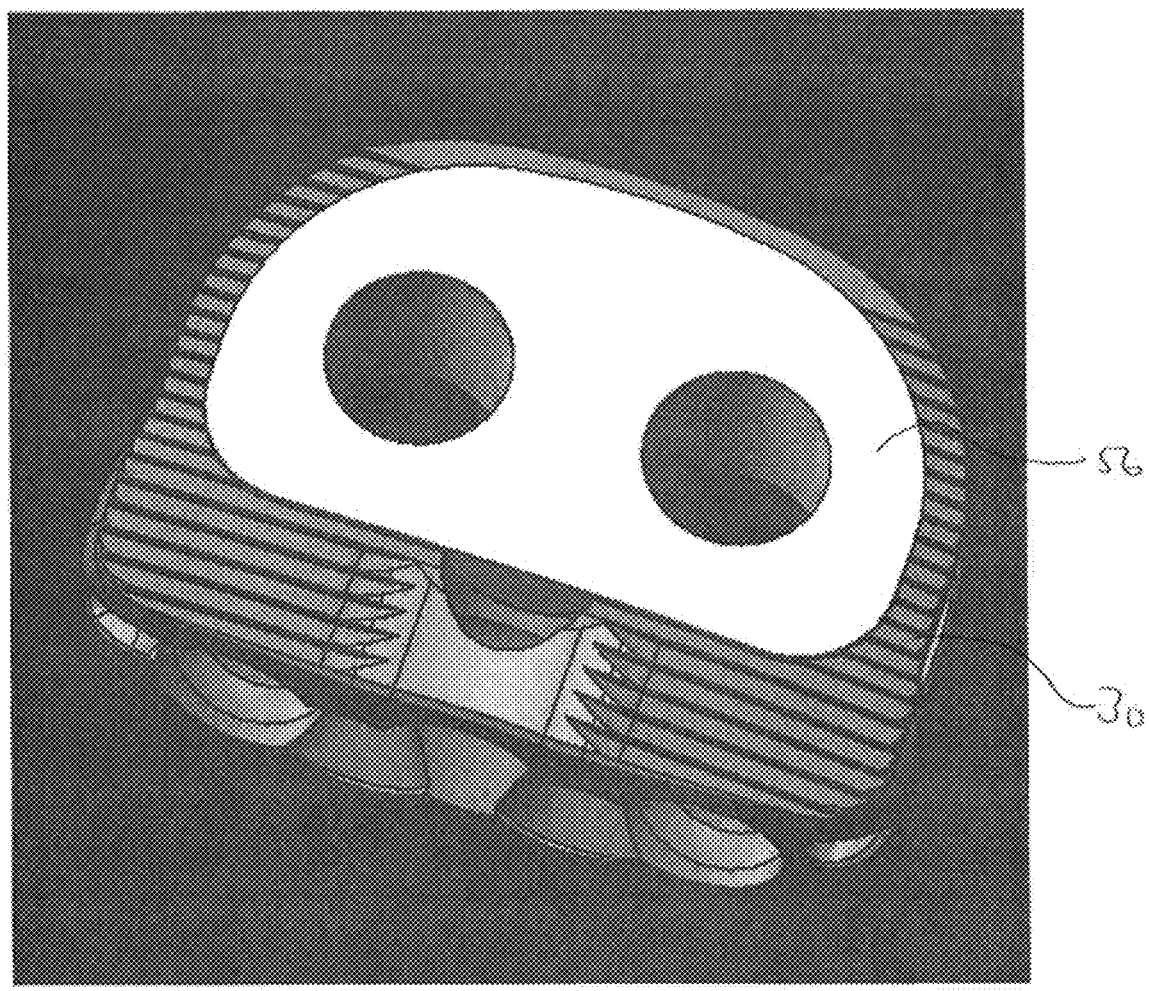
FIG. 19 is the frame or cage depicted in FIG. 6 where the compressed or molded implant has a solid construction with multiple openings configured to receive plugs of bone graft material.

FIG. 6 shows one example of a frame or cage 30, which may be suitable for retaining compressed or molded implant 32 in solid form having an opening 34 configured to receive a plug of bone graft material. FIG. 11 shows the frame or cage 30 where the compressed or molded implant 44 has a single piece construction in solid form without any openings or notches. FIG. 12 is the frame or cage 30 where the solid compressed and/or molded implant 46 includes multiple notches each configured to receive a portion of fastener, such as a bone screw (not shown). FIG. 13 is the frame or cage 30 where the solid compressed and/or molded implant 48 has an opening with a plug 50 of bone graft material received therein. The plug 50 may be comprised of the same or different material than the implant 48. FIG. 14 is an exploded view of the plug 50, the implant 48, and the frame 30. FIG. 15 is an exploded view of the implant 48 and the frame 30 with the plug removed. FIG. 16 shows the assembled version of FIG. 15 with the frame 30 having the implant 48 received therein with the plug removed. FIG. 18 depicts the frame 30 retaining compressed and/or molded implant 54 having a solid construction with an elongated central opening which mimics the outside shape of the implant 54. FIG. 19 depicts the compressed or molded implant 56 having multiple openings configured to receive one or more plugs of bone graft material.

Figure 7:
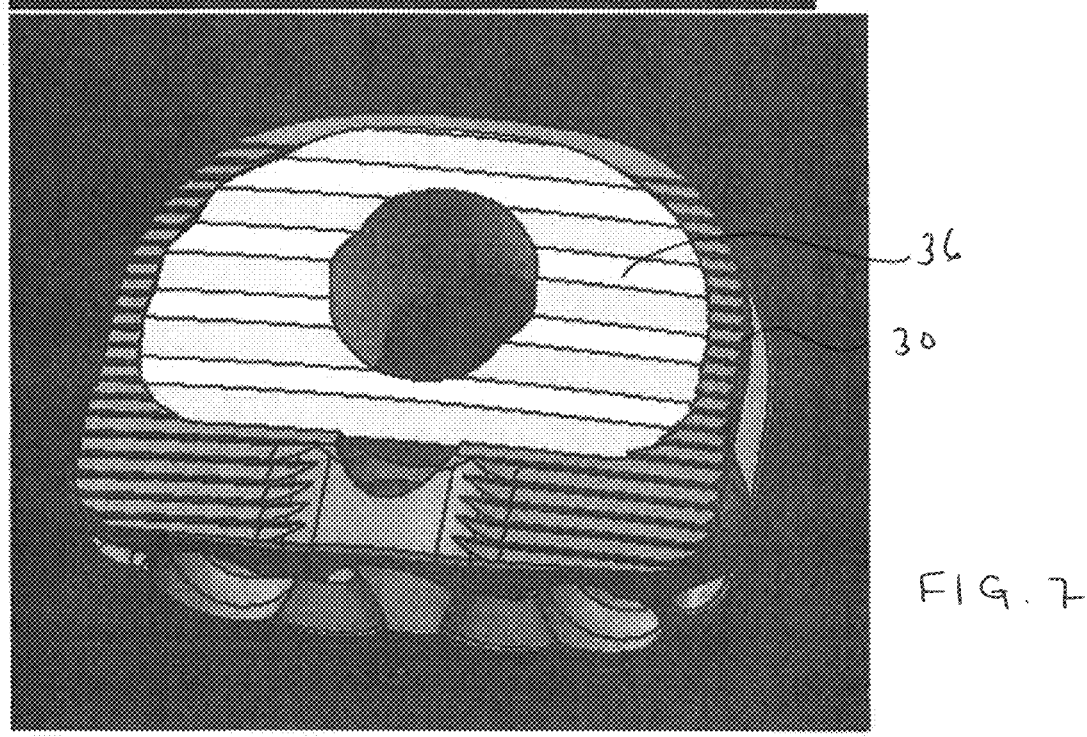
FIG. 7 shows the frame or cage depicted in FIG. 6 where the compressed or molded implant is comprised of multiple layers having an opening configured to receive a plug of bone graft material.
Figure 8:
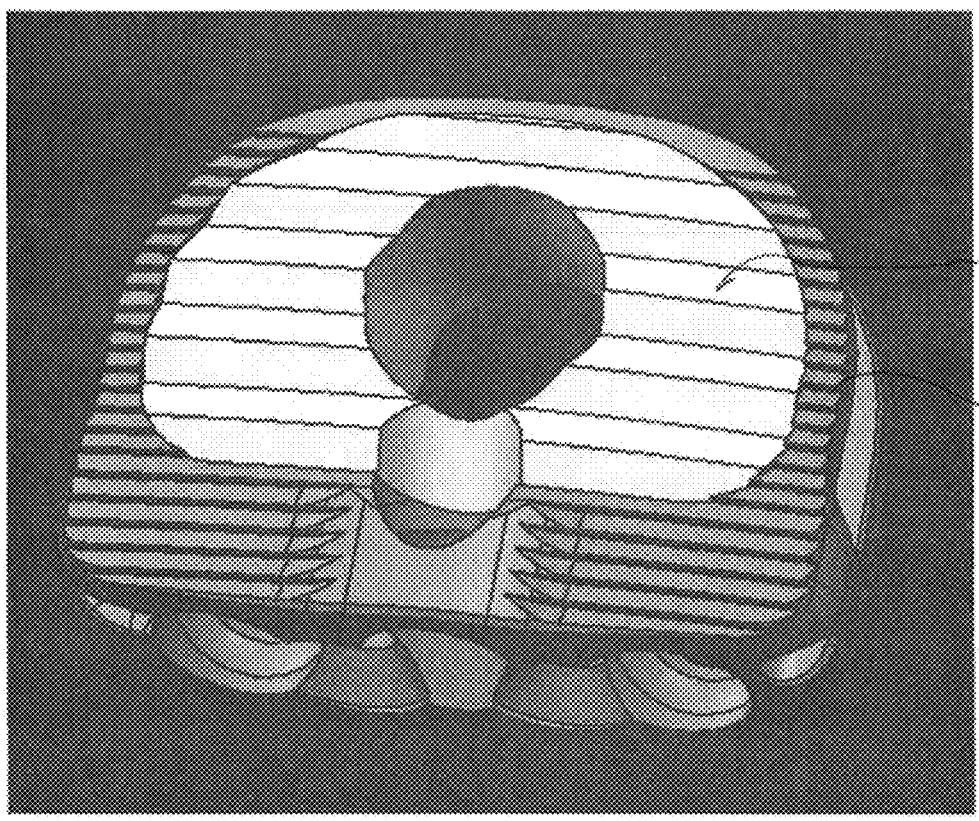
FIG. 8 is the frame or cage depicted in FIG. 6 where the multi-layered compressed or molded implant having an opening configured to receive a plug of bone graft material also includes a notch configured to receive a portion of a bone screw.
Figure 9:
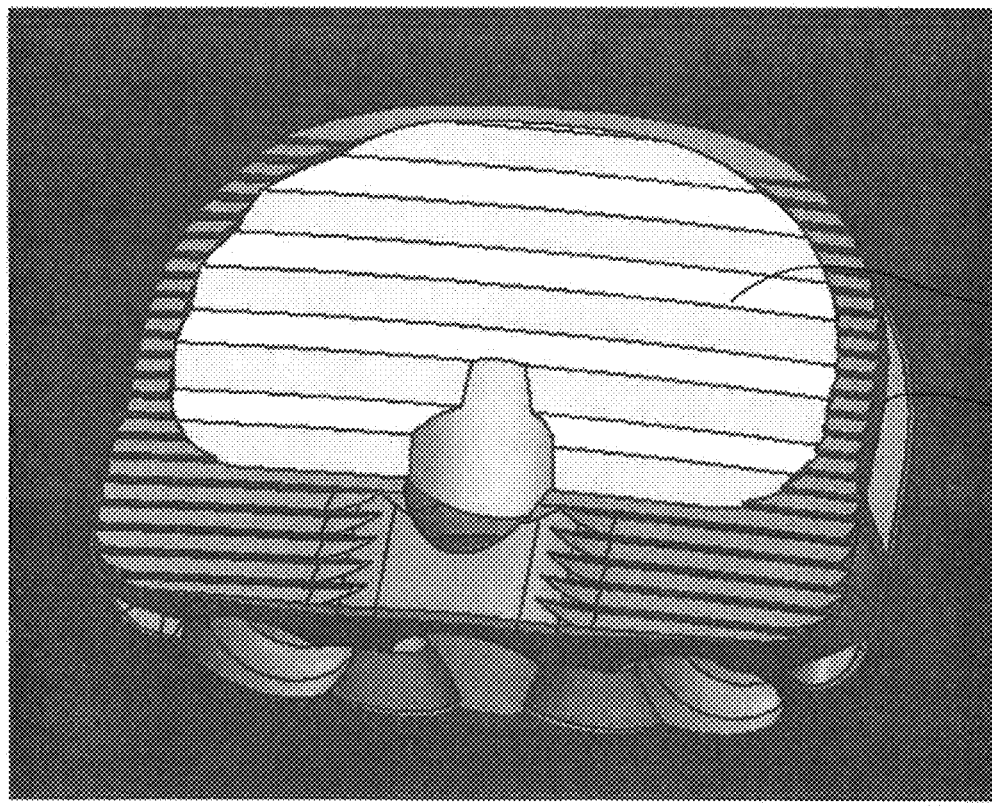
FIG. 9 is the frame or cage depicted in FIG. 6 where the multi-layered compressed or molded implant is in solid form, but includes a notch configured to receive a portion of a bone screw.
Figure 10:
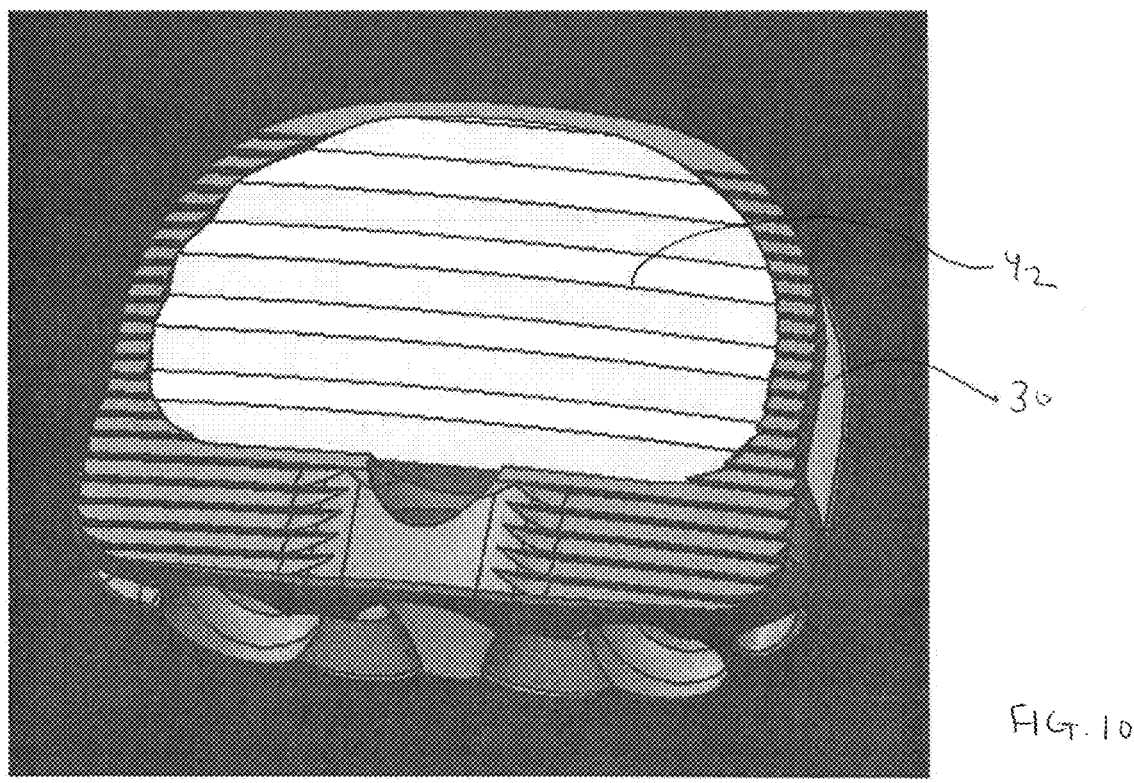
FIG. 10 shows the frame or cage depicted in FIG. 6 where the multi-layered compressed or molded implant is in solid form with no openings therein.
Figure 17:
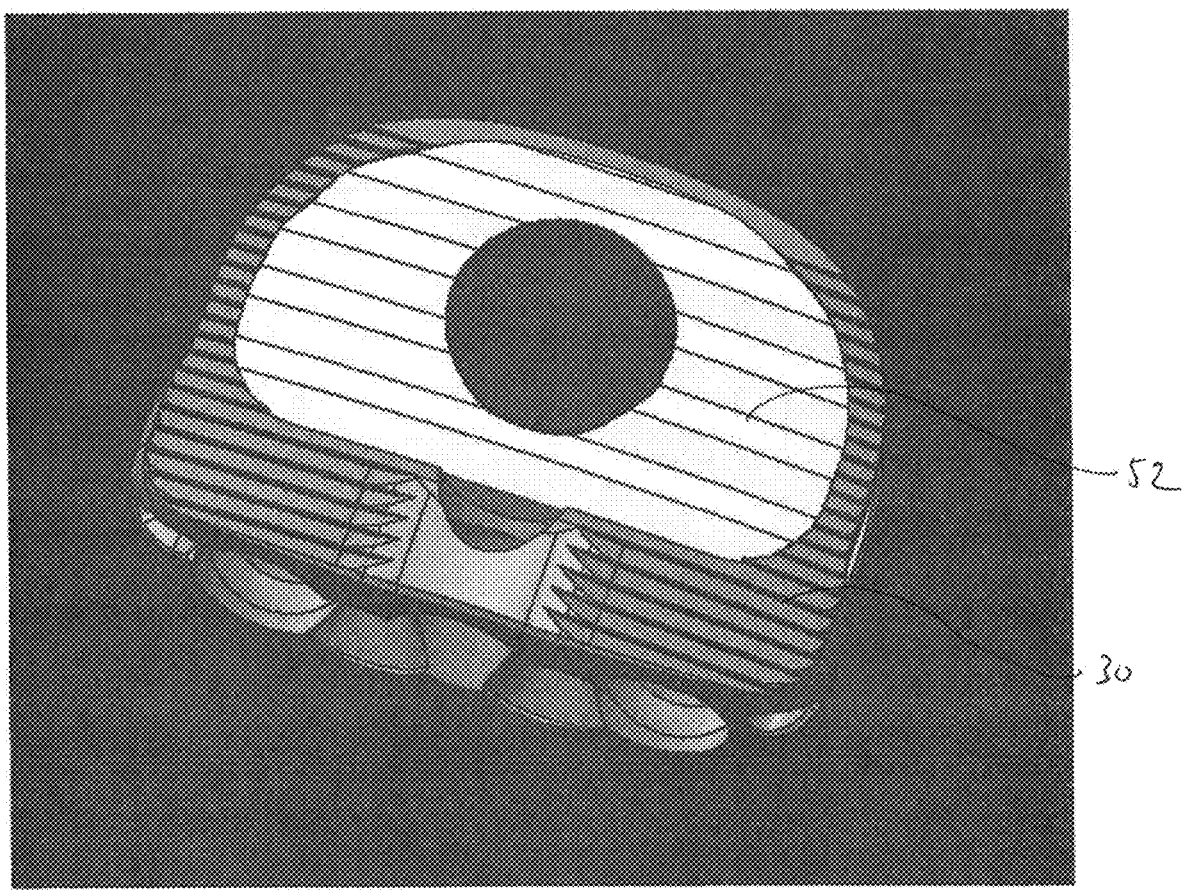
FIG. 17 depicts the frame or cage depicted in FIG. 6 where the compressed or molded implant has a multi-layered construction with an opening configured to receive a plug of bone graft material.

The implants or a portion thereof may also be prepared using a layered technique. For example, multiple layers of the demineralized bone composition may be layered, for example, in a mold to create the implant. Each layer may consist of the same or a different material. For example, the layered composite may include alternating layers of different compositions. FIG. 7 shows the frame or cage 30 including a compressed and/or molded implant 36 which is comprised of multiple layers and having an opening configured to receive a plug of bone graft material. FIG. 8 shows a version of the multi-layered compressed and/or molded implant 38 having an opening configured to receive a plug of bone graft material and a notch configured to receive a portion of a bone screw. FIG. 9 shows a version of the multi-layered compressed and/or molded implant 40 having a notch configured to receive a portion of a bone screw. FIG. 10 shows a version of the multi-layered compressed and/or molded implant in a solid form without openings or notches. FIG. 17 depicts the frame 30 retaining compressed and/or molded implant 52, which has a multi-layered construction with an opening configured to receive a plug of bone graft material.

The biomaterials and implants formed therefrom described herein are intended to be applied at a bone repair site, e.g., one resulting from injury or defect. The implants can be utilized in a wide variety of orthopedic, periodontal, neurosurgical, oral and maxillofacial surgical procedures. In particular, the biomaterials may be suitable for repairs of the vertebral column including spinal fusion and internal fixation; tumor surgery, e.g., deficit filling; discectomy; laminectomy; scoliosis, lordosis and kyphosis treatments. Possible clinical applications may include e.g., the treatment of spinal disc degeneration or disease, traumatic, pathologic, or stress fractures, congenital defects or fractures, or operative defects in any bone or between bones of the body.

The compositions and implants may be configured for use at various target repair sites within a body of a patient to facilitate bone growth therein. In some embodiments, the composition is configured for use at a target repair site in the patient's spine. For example, the composition can facilitate growth of bone between the body of a first vertebra and the body of a second vertebra to achieve interbody fusion of the two vertebrae. In a spinal fusion procedure, the composition may be used in conjunction with one or more mechanical supports (e.g., a cage or frame, spacer, plate, a plurality of screws and/or rods, or the like). Although the spine is described, the composition can be configured to be implanted into or at a target repair site in or at a different bone or bony structure of the patient's body.

The term "treating" and the phrases "treatment of a disease" and "treatment of a condition" refer to executing a protocol that may include the use of the compositions, devices and methods herein and/or administering one or more biomaterials to a patient (human, normal or otherwise, or other mammal), in an effort to alleviate signs or symptoms of the disease or condition. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms and does not require a cure to the ailment.

Further example embodiments are directed to kits that include components for making the present biomaterials and implants, including for example, carriers or scaffolds, cages (e.g., titanium and/or polyether ether ketone (PEEK) spacers), allograft spacers, demineralized bone materials, cell culture media, phosphate buffered saline (PBS), a tissue culture substrate such as a flask, trypsin, or mixtures, bone graft harvesting tools, bone marrow aspirate retrieval tools, or the like. Additional components, instructions and/or apparatus' may also be included.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLE

In this example, a bioactive ceramic scaffold is made using tricalcium phosphate, a bioactive glass, and collagen. Putty and strip formulations were developed as provided in the table below:

|  | Putty | Strip |
| --- | --- | --- |
| TCP | 60-70% (w/w) | 55-65% (w/w) |
| Bioactive glass | 15-20% (w/w) | 10-20% (w/w) |
| Collagen | 6-10% (w/w) | 12-15% (w/w) |
| Hyaluronic Acid | up to 2% (w/w) | less than 1% (w/w) |

First, the collagen and hyaluronic acid were mixed in hydrochloric acid and allowed to swell at 4° C. for up to 24 hours. At the end of the swelling, the mixture was combined with TCP and bioactive glass and mixed thoroughly. In the case of the strips, the mixture was poured into molds, frozen, and freeze-dried. The freeze-dried strips were crosslinked using a formaldehyde crosslinking agent and residual formaldehyde was removed with rinsing in deionized water. The final products were sterilized using ethylene oxide. The putty was moldable and the strips were flexible. The putty and strips exhibited osteoconductive and osteostimulative properties, which aids in bone regeneration.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various materials, implants, and devices disclosed above may be combined or modified in any suitable configuration.

What is claimed is:

1. A method of making an implantable biomaterial for aiding bone regeneration, the method comprising:
obtaining demineralized bone in particulate form including demineralized cortical fibers having a fiber length from 250 μm to 750 μm;
mixing the demineralized, particulate bone with a hydrogel carrier including only a mixture of hyaluronic acid and hydrochloric acid to form a demineralized, particulate bone mixture, adding the demineralized, particulate bone mixture including the demineralized cortical fibers to a mold;

compressing the demineralized, particulate bone mixture in the mold for a time and pressure sufficient to form a molded biomaterial composition of a given shape, wherein the pressure is between 15 psi to 50 psi;

freeze-drying the molded biomaterial composition to form a freeze-dried biomaterial; and cross-linking the freeze-dried biomaterial with a monoaldehyde to form the implantable biomaterial, wherein the shape of the implantable biomaterial is determined by the mold and wherein the shape of the implantable biomaterial is suitable for implantation.

2. The method of claim 1 further comprising adding bioactive glass, tricalcium phosphate, or a combination thereof to the demineralized, particulate bone.

3. The method of claim 1, wherein the demineralized bone further includes demineralized cancellous fibers.

4. The method of claim 1, wherein the implantable biomaterial includes a plurality of complimentary shapes assembled together.

5. The method of claim 4, wherein the plurality of complimentary shapes include a first portion having a mortise interlocked with a second portion having a tenon received in the mortise of the first portion.

6. The method of claim 4, wherein the plurality of complimentary shapes include a plurality of substantially concentric rings interlocked together, the concentric rings including a first ring positioned entirely inside a second ring.

7. The method of claim 1, wherein the implantable biomaterial includes one or more openings sized and configured to receive one or more bone graft materials.

8. The method of claim 1, wherein the implantable biomaterial includes one or more notches configured to receive a portion of a bone fastener.

9. The method of claim 1, wherein the implantable biomaterial is sized and dimensioned to be retained within a cage, and the implantable biomaterial has an opening configured to receive a plug of bone graft material.

10. A method of making an implantable biomaterial for aiding bone regeneration, the method comprising:

mixing 10-60% w/w of demineralized bone in particulate form including demineralized cortical fibers having a fiber length from 250 μm to 750 μm, 10-40% w/w of non-porous tricalcium phosphate having a particle size ranging from 100 to 250 μm, 10-40% w/w of bioactive glass having a particle size ranging from 75 to 500 μm; and 1-20% w/w of hydrogel carrier to form a mixture, the hydrogel carrier includes hyaluronic acid mixed in hydrochloric acid;

adding the mixture to a mold;

compressing the mixture in the mold for a time and pressure sufficient to form a molded biomaterial composition of a given shape, wherein the pressure is between 15 psi to 50 psi;

freeze-drying the molded biomaterial composition to form a freeze-dried biomaterial; and cross-linking the freeze-dried biomaterial with a monoaldehyde to form the implantable biomaterial, wherein the shape of the implantable biomaterial is determined by the mold and wherein the shape of the implantable biomaterial is suitable for implantation.

11. The method of claim 10, wherein the implantable biomaterial includes a plurality of complimentary shapes assembled together.

12. The method of claim 11, wherein the plurality of complimentary shapes include a first portion having a mortise interlocked with a second portion having a tenon received in the mortise of the first portion.

13. The method of claim 11, wherein the plurality of complimentary shapes include a plurality of substantially concentric rings interlocked together.

14. The method of claim 10, wherein the implantable biomaterial includes one or more openings sized and configured to receive one or more bone graft materials.

15. The method of claim 10, wherein the implantable biomaterial includes one or more notches configured to receive a portion of a bone fastener.

16. The method of claim 10, wherein the implantable biomaterial is sized and dimensioned to be retained within a cage, and the implantable biomaterial has an opening configured to receive a plug of bone graft material.

17. The method of claim 10, wherein the implantable biomaterial includes a biological agent including bone morphogenic protein (BMP), stem cells, or a bone growth factor.

18. The method of claim 1, wherein the monoaldehyde is formaldehyde, acetaldehyde, or glutaraldehyde.

* * * * *